United States Patent [19]

Bodo et al.

[11] Patent Number: 5,196,323

[45] Date of Patent: Mar. 23, 1993

[54] PROCESS FOR PREPARING AND PURIFYING ALPHA-INTERFERON

[75] Inventors: Gerhard Bodo; Ingrid Maurer-Fogy; Edgar Falkner, all of Vienna; Silvia J. Lindner, Perchtoldsdorf, all of Austria

[73] Assignee: Boehringer Ingelheim International GmbH, Ingelheim am Rhein, Fed. Rep. of Germany

[21] Appl. No.: 713,618

[22] Filed: Jun. 12, 1991

Related U.S. Application Data

[63] Continuation of Ser. No. 856,333, Apr. 28, 1986, abandoned.

[30] Foreign Application Priority Data

Apr. 27, 1985 [DE] Fed. Rep. of Germany ....... 3515336

[51] Int. Cl.$^5$ .......................... C07K 13/00; C07K 3/28; C07K 3/22; C07K 3/24
[52] U.S. Cl. .................................. 435/69.51; 530/351; 530/413; 530/416; 530/419; 424/85.4; 424/85.7; 435/252.3
[58] Field of Search ................. 530/351, 413, 416, 419; 424/85.4, 85.7; 435/69.51

[56] References Cited

U.S. PATENT DOCUMENTS

| | | | |
|---|---|---|---|
| 4,364,863 | 12/1982 | Leibowitz et al. | 424/85.7 |
| 4,496,537 | 1/1985 | Kuan | 424/85.7 |
| 4,535,906 | 8/1985 | Johnston | 424/85.7 |
| 4,680,260 | 7/1987 | Debabov et al. | 435/69.51 |

FOREIGN PATENT DOCUMENTS

| | | |
|---|---|---|
| 0018218 | 10/1980 | European Pat. Off. . |
| 0043980 | 1/1982 | European Pat. Off. . |
| 0108585 | 5/1984 | European Pat. Off. . |
| 0110302 | 6/1984 | European Pat. Off. . |
| 3306060 | 8/1984 | Fed. Rep. of Germany . |
| 3432196 | 3/1986 | Fed. Rep. of Germany . |
| 2079291 | 1/1982 | United Kingdom . |

OTHER PUBLICATIONS

Hitzman et al. (1983) Science 219, 620–625.
Zwanthoff et al. (1985) J. Gen. Virol. 66, 685–691.
Staehelin et al., *J. Bio. Chem.* 256:9750–9754 (1981).
Protzman et al., *J. Immunol. Methods* 75:317–323 (1984).
Wetzel et al., *J. Interferon Res.* 1:381–390 (1981).
Copy of European Search report for European Application Publication No. 203382.
Antonelli, G. et al., *JID*:163:882–885 (1991).
Inglada, L. et al., *The Lancet*, p. 1521, Dec. 26, 1987.
von Wussow, P. et al., *The Lancet*, pp. 635–636, Sep. 12, 1987.

*Primary Examiner*—Robert A. Wax
*Assistant Examiner*—R. Keith Baker
*Attorney, Agent, or Firm*—Sterne, Kessler, Goldstein & Fox

[57] ABSTRACT

A process for the preparation and purification of recombinant Interferon-α is disclosed. The invention is directed to a process comprising the following steps: cultivating *E. coli* containing the interferon gene for a growth period during which not more than 5% methionine-interferon is formed; extracting and concentrating the expressed interferon; subjecting the preliminarily purified material to Tandem Chromatography, wherein the Tandem Chromatography comprises separation on a cellulose column followed by an anti-alpha-interferon monoclonal antibody affinity column; subjecting the thus purified material to isoelectric precipitation of impurities at about pH 4.0 to about pH 4.8; and purifying the interferon by chromatography on a high performance cation exchange column using a volatile buffer, wherein the purified interferon is non-immunogenic when administered parenterally to a human.

8 Claims, 17 Drawing Sheets

MALIGNANT APUDOMA 1

BRONCHIAL-CA 1 
(2)

0 2 4 6 8 10 12 14 16 18 20 WEEKS

SCLERODERM 1

PAP. CUTIS CARCIN. GUTTRON 1

0 2 4 6 8 10 12 14 16 18 20 WEEKS

FIG. 13a

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   |   |   |   |   |   |   |   |   |    |    |    |
| C |   |   |   | (= 12 IU/ml) | (= 6 IU/ml) | (= 3 IU/ml) | (= 1.5 IU/ml) | (= 0.75 IU/ml) | (= 0.38 IU/ml) |    |    |    |
| D |   |   |   |   |   |   |   |   |   |    |    |    |
| E |   |   |   |   |   |   |   |   |   |    |    |    |
| F |   |   |   | 1: 1.000 | 1: 2.000 | 1: 4.000 | 1: 8.000 | 1: 16.000 | 1: 32.000 |    |    |    |
| G |   |   |   |   |   |   |   |   |   |    |    |    |
| H |   |   |   |   |   |   |   |   |   |    |    |    |
|   |   | R | V | _____ HS-11 _____ | | | | | | R | V |   |

R = CELL BLIND VALUE
V = VIRUS CONTROL

FIG. 13b

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   |   |   |   |   |   |   |   |   |    |    |    |
| C |   |   |   |   |   |   |   |   |   |    |    |    |
| D |   |   |   |   |   |   |   |   |   |    |    |    |
| E |   |   |   |   |   |   |   |   |   |    |    |    |
| F |   |   |   | 1: 2 | 1: 4 | 1: 8 | 1: 16 | 1: 32 | 1: 64 |    |    |    |
| G |   |   |   |   |   |   |   |   |   |    |    |    |
| H |   |   |   |   |   |   |   |   |   |    |    |    |
|   |   | R | V | _____ HS-11 + SAMPLE _____ | | | | | | R | V |   |

PROCESS FOR PREPARING AND PURIFYING ALPHA-INTERFERON

This application is a continuation of application Ser. No. 06/856,333, filed Apr. 28, 1986, now abandoned.

BACKGROUND OF THE INVENTION

1. The Field of the Invention

The present invention relates to a process for preparing a very pure, non-immunogenic, homogeneous alpha-interferon having antiviral and immunoregulatory activity, the protein itself and the use thereof.

2. The Background Art

Interferons are proteins naturally ocurring in the body which may be detected in a great variety of species. The antiviral and immunoregulatory properties inherent in them indicated at an early stage that they might be suitable for a wide variety of applications. Tests have shown that there are different classes of interferon. In addition to alpha, beta and gamma interferons, omega-interferon has recently been discovered and its structure clarified.

The high expectations placed on the interferons as an effective agent against viral diseases and cancer have already lead to trials with interferon preparations obtained from natural material, but serious side effects occurred. The preparations used in these trials, even after laborious purification, contained complex mixtures of different interferons and, in many cases, other proteins. The reason for this is that some of the interferons have subtypes differing from one another to a greater or lesser extent; thus, for example, more than 20 different types of alpha-interferon are known.

Only by producing interferons by genetic engineering has it been possible to conduct trials with pure types of interferon preparations.

These also include the recombinant alpha$_2$ interferons used in the clinical trials (also known as alpha A). The purification of the proteins is of critical importance to the production of human proteins by microorganisms. Any contamination originating from the host organism would lead to immune defense reactions if the product were to be used in humans and these could be life threatening. However, nowadays, the removal of contaminants of this kind presents scarcely any problems and the extremely sensitive analytical methods now available will detect endotoxins in very tiny concentrations. In the field of interferon research too, methods of purification have been developed with which interferon preparations containing virtually no endotoxins can be obtained. Mention may be made, for example, of the work of Staehelin et al., J. Biol. Chem. 256, 9750 (1981).

In addition, recombinant alpha-interferons used in clinical trials are virtually free from endotoxins.

It was, therefore, all the more surprising that side effects were encountered that were severe enough to require discontinuation of interferon treatment. Some recombinant alpha-interferons were, surprisingly, found to be immunogenic; antibodies against interferon had been stimulated (Quesada et al., J. Natl. Cancer Inst. 70, No. 6, 1041-1046 (1983); Protzman et al., J. Immunol. Methods 75, 317-323 (1984)).

These antibodies may lead to serious effects if they influence the action of the interferon. This is because they act, not only on the recombinant alpha-interferon, but, as the recombinant alpha-interferon is identical to the body's own interferon, on the body's own interferon as well.

The disastrous aspect of this is that these antibodies go on acting even after the interferon treatment has ended. The antibodies may cause a deterioration during the course of the disease, weakening the body's own defenses against virus infections, and thus making the organism even more susceptible to other infections.

These effects have already been confirmed in tests on animals. Therefore, with a view to maximum safety of drug treatment, it is essential that the recombinant alpha$_2$ interferon must be pure and virtually free from endotoxins and non-immunogenic.

The cause of the immunogenicity of the abovementioned alpha-interferons is not known. All that is clear is that endotoxic contaminants are not responsible.

The preparations of alpha-interferon that have been used for trials differ primarily in slight variations in the basic amino acids at positions 23 and 34:

|  | Amino acid 23 | Amino acid 34 |
|---|---|---|
| Preparation I: | Lysine | Histidine |
| Preparation II: | Arginine | Histidine |
| Preparation III: | Arginine | Arginine |

In addition, the differences in the primary structure of the proteins used in clinical trials, it is well known that the alpha-interferons produced by genetic engineering always consist of a mixture of monomeric, shortened-molecular, reduced and oligomeric forms of interferon (see, for example, EPA 108 585, 110 302 and 118 808). Some of these forms show the same activities in vitro, but others show reduced activities and some are reputed to have possible immunogenic properties (see EPA 108 585 and 110 302).

These patent applications describe processes for separating these forms of interferon.

EPA 108 585 describes a process for separating a "slow moving monomer" and oligomers wherein the interferon probe is incubated at a temperature of 28°-40° C. for some time at a pH of 3 to 5.

EPA 110 302 describes a process wherein the monomer is formed from the oligomers by reduction with a redox system.

Finally, in EPA 118 808, recombinant alpha-interferon is purified with the aid of metal chelate resins from the oligomeric forms.

The interferons obtained by these methods are claimed to contain monomeric interferon in virtually quantitative form; however, there are no tests for immunogenicity reported in these documents.

SUMMARY OF THE INVENTION

The aim of this invention is to develop a process for preparing a non-immunogenic recombinant alpha-interferon with antiviral and immunoregulatory activities.

The invention relates to a process for preparing recombinant alpha-interferon which is pure, virtually free from endotoxins, and non-immunogenic. The method is suitable for the preparation and purification of alpha-interferons from different species, such as human or animal alpha-interferons. The host organism used for the preparation may be a prokaryote or eukaryote, e.g., E. coli or Saccharomyces cerevisiae, preferably E. coli. The conditions of cultivation for the various host organisms are well known to those skilled in the art.

The invention further relates to a process for preparing recombinant alpha-interferon which is homogeneous, pure, solid, non-immunogenic, free from reduced forms and fragments. Further, these recombinant alpha-interferons contain at most small amounts of oligomer, dimer/trimer/tetramer, and methionine interferon. Additionally, the recombinant alpha-interferon is predominantly native monomeric alphainterferon.

Figure 1:
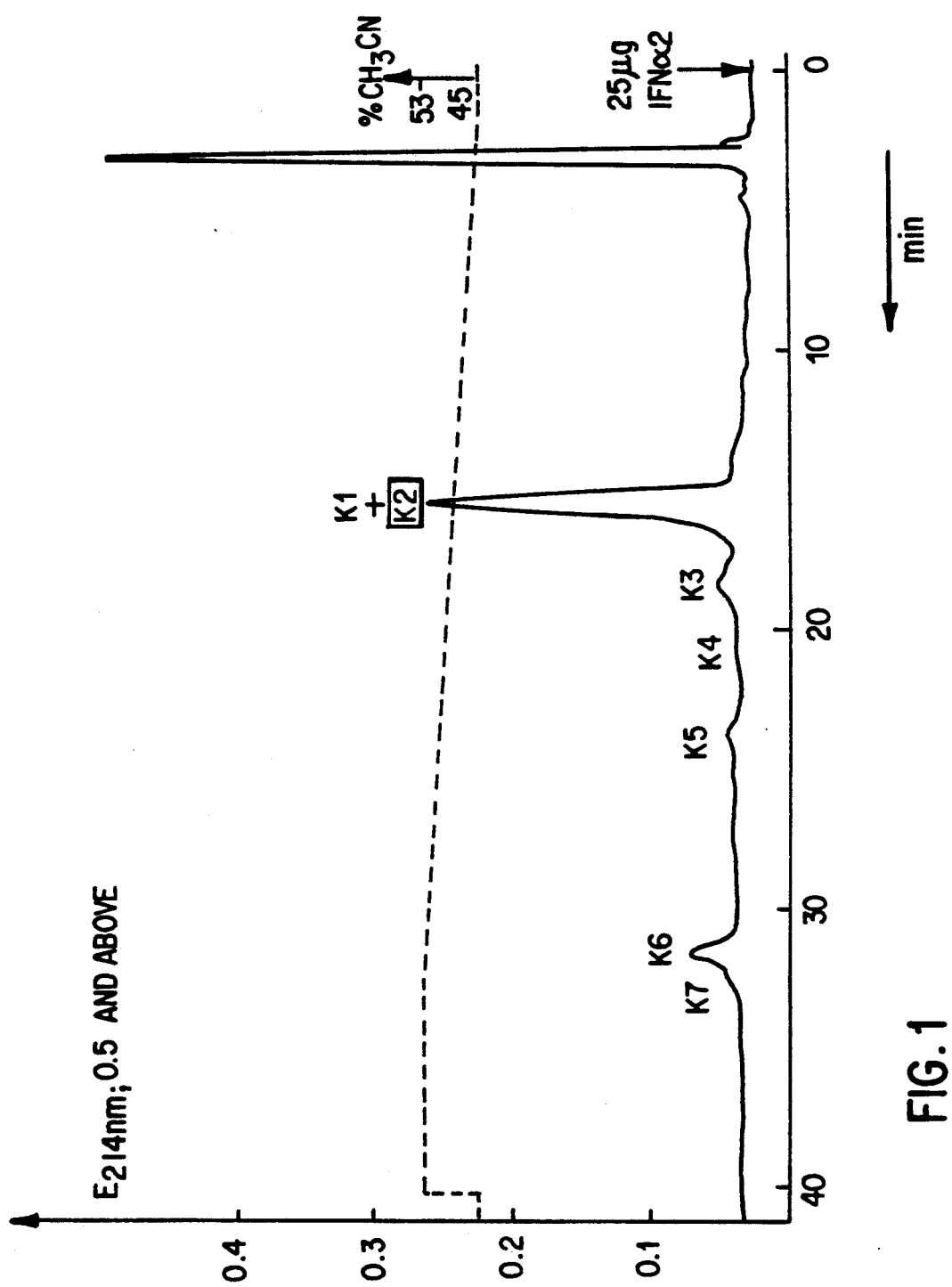
FIG. 1 shows a chromatograph of reverse phase HPLC of the acid eluate after Tandem Chromatography. Components K1-K7 are shown as peaks.

| Total number of patients: | 75 |
| --- | --- |
| Number of patients with tumor indications: | 58 |
| Number of patients without stimulated antibodies: | 58 |
| Number of patients with virus indications: | 17 |
| Number of patients without stimulated antibodies: | 17 |

FIG. 13 is a diagram of the anti-interferon-alpha antibody assay used in FIGS. 12a-12f.

Table 1 (a) is a summary of the purification steps for alpha-interferon.

Table 2 (b) is a summary of purity by HPLC of the various alpha-interferon components relative to that of K1+K2.

DESCRIPTION OF THE PREFERRED EMBODIMENTS

Our own detailed analytical investigations have shown that alpha-interferons prepared by recombinant methods are a mixture of different forms of interferon in fluctuating concentrations.

These include oligomers, tetramers, trimers and dimers of interferon, methionine interferon, reduced forms and fragments of interferon and, surprisingly, various monomeric forms of interferon as well.

The "oligomers" are alpha-interferons with a molecular weight >70,000. The "reduced" alpha-interferons are the protein with free sulfhydryl groups, and the "methionine" interferon is an alpha-interferon which additionally carries a methionine at the N-terminal end (caused by the microbiological method of biosynthesis of alpha-interferon).

Analysis has shown that the various "monomeric" forms are different disulfide isomers of alpha-interferon.

In order to distinguish between these isomers linguistically, the term "non-native monomer" will be used hereafter for the isomers of the predominantly occurring alpha-interferon monomer, and the latter will be referred to as native "monomeric" alpha-interferon. However, this should not exclude the possibility that the non-native monomers may also exist in "natural" material.

In an E. coli fermentation mixture for preparing alpha$_2$ interferon, for example, seven different interferon components could be detected (K1-K7).

Analysis showed that these were oligomers, dimers and trimers, methionine interferon, reduced interferons and a disulfide isomer of native monomeric alpha$_2$ interferon which had a disulfide bridge between the amino acids at positions 1 and 98 and 29 and 138 (see also, Wetzel et al., J. Interferon Res. 1, No. 3, 381-391 (1981)).

As already stated, the reason for the immunogenicity of recombinant alpha-interferon is not known. However, it is obvious that all forms of alpha-interferon that differ from the body's own interferon have potential immunogenic activity. These forms include the shortened molecules, the dimers and oligomers, and also the non-native monomers which contain differently-linked disulfide bridges.

As long as the causes of immunogenicity are not yet clear, no conditions which might promote the formation of these forms with their unknown effects should be used in processes for preparing recombinant alpha-interferons. This means that even the purification of interferon must be carried out under the mildest possible conditions which would not endanger nativity. Elevated temperatures and reducing agents should not be employed.

Obviously, efforts must be made during all steps of the purification to ensure that no foreign substances are introduced, for example, as a result of the use of metal chelate resins or similar problematic reagents.

Surprisingly, it has been found that the growth time not only affects the yield of alpha-interferon but is also a crucial factor in determining the critically important composition of the interferon mixture. Thus, if E coli is used, the composition of the interferon mixture changes with regard to the quantity of contaminating methionine inteferon, depending on the duration of growth.

It is desirable, therefore, that the fermentation mixture be tested at short intervals for the formation of alpha-interferon derivatives produced by the host organism, as an indicator of the best growth time. Methionine interferon may be used as an indicator of this kind. Therefore, by discontinuing the process at the appropriate time, for example, after the formation of less than 20%, preferably less than 5%, more particularly less than 1% of methionine interferon, a particularly pure interferon is obtained with ideal prerequisites for the subsequent purification process according to the invention.

The process is particularly suitable for the preparation of acid-stable alpha-interferon. For example, the process according to DE 34 32 196.9, wherein the cells with a pH of 2 are destroyed in a homogenizer, may be used.

The invention relates to Tandem Chromatography, i.e. successive chromatographic stages using different adsorption agents with suitable washing and eluting solutions (details below), by which, surprisingly, the majority of the impurities can be removed. Preferably, a combination of a cellulose preliminary column in series with an affinity column is used. It is particularly preferred to use a DE-52 cellulose primary column in tandem with a monoclonal anti-interferon IgG-antibody, such as, for example, the EBI 1 antibody described in DE-OS 33 06 060, coupled to a carrier such as Sepharose.

A Tris/NaCl buffer pH 7.5 has proved suitable as a washing solution, but it is also possible to use other column washing solutions that do not affect the binding of the interferon to the antibody, but that elute the contaminants and leave those constituents which have a negative effect on the properties of the antibody column bound to the preliminary column.

A suitable eluant for interferon is, for example, a buffer solution consisting of 0.1M citric acid in 25% ethylene glycol, but other eluants having similar properties are also suitable. In general, the eluant must be matched to the particular alpha-interferon which is to be purified.

Some of the impurities in the "tandem eluate" could, surprisingly, be removed by buffering the pH to 4.0–4.8, more preferably pH 4.5. The pH value should be selected so that there is as little monomeric alpha-interferon as possible in the precipitate. Final purification of the interferon is achieved by chromatography using a cation exchanger, preferably a MONO-S, type HR 10/10 cation exchanger. A flat graduated gradient with a volatile buffer such as ammonium acetate buffer, in which the pH was kept constant and the concentration was varied (concentration gradient), was used to elute the highly purified alpha-interferon. It would be equally possible to keep the concentration constant and vary the pH (pH gradient). The crucial point is that the eluant should be capable of removing any interferon contaminants, particularly any of the disulfide isomers of the main monomer. A linear concentration gradient of an ammonium acetate buffer produced from 0.1 to 1.0M, preferably 0.1 to 0.5M ammonium acetate, in a pH range of from 4.0 to 5.0, preferably pH 4.5, is particularly suitable for this purpose. This buffer can, moreover, be removed by lyophilization so that the highly purified alpha-interferons can be obtained for the first time in solid form free from buffer salts and precipitation agents.

The process according to the invention is particularly suitable for the preparation of pure alpha-interferons of various species which do not stimulate any antibodies when administered to the corresponding species.

The process according to the invention has proved particularly advantageous in the preparation of a recombinant, homogenous, pure, solid and non-immunogenic alpha-interferon which is free from reduced forms and fragments of interferon, which contains less than 0.2% oligomer and wherein more than 90% of the monomer content consists of native monomeric alpha-interferon.

The process according to the invention may be used particularly advantageously for the preparation of an alpha-interferon as described above wherein the host organism contains the gene that codes for human alpha-interferon according to the amino acid sequence:

| Cys | Asp | Leu | Pro | Gln | Thr | His | Ser | Leu | Gly | Ser |
| Arg | Arg | Thr | Leu | Met | Leu | Leu | Ala | Gln | Met | Arg |
| Arg | Ile | Ser | Leu | Phe | Ser | Cys | Leu | Lys | Asp | Arg |
| Arg | Asp | Phe | Gly | Phe | Pro | Gln | Glu | Glu | Phe | Gly |
| Asn | Gln | Phe | Gln | Lys | Ala | Glu | Thr | Ile | Pro | Val |
| Leu | Hi | Glu | Met | Ile | Gln | Gln | Ile | Phe | Asn | Leu |
| Phe | Ser | Thr | Lys | Asp | Ser | Ser | Ala | Ala | Trp | Asp |
| Glu | Thr | Leu | Leu | Asp | Lys | Phe | Tyr | Thr | Glu | Leu |
| Tyr | Gln | Gln | Leu | Asn | Asp | Leu | Glu | Ala | Cys | Val |
| Ile | Gln | Gly | Val | Gly | Val | Thr | Glu | Thr | Pro | Leu |
| Met | Lys | Glu | Asp | Ser | Ile | Leu | Ala | Val | Arg | Lys |
| Tyr | Phe | Gln | Arg | Ile | Thr | Leu | Tyr | Leu | Lys | Glu |
| Lys | Lys | Tyr | Ser | Pro | Cys | Ala | Trp | Glu | Val | Val |
| Arg | Ala | Glu | Ile | Met | Arg | Ser | Phe | Ser | Leu | Ser |
| Thr | Asn | Leu | Gln | Glu | Ser | Leu | Arg | Ser | Lys | Glu | and the native monomeric alpha-interferon contains disulfide bridges between the cysteines at positions 1 and 98 and 29 and 138.

This invention also relates to recombinant alpha-interferons that can be prepared using the process according to the invention, preferably recombinant alpha-interferons in homogeneous pure form which contain less than 20%, preferably less than 5%, more particularly less than 1% of methionine interferon.

Depending on the choice of host organism and the nature of the fermentation conditions, alpha-interferons prepared by the recombinant method may contain, in addition to methionine interferon, di- tri-, tetra-and oligomers, reduced forms and fragments and disulfide isomers of the predominantly occurring monomeric alpha-interferon in fluctuating quantities which can be suppressed or eliminated for the first time using the process according to the invention.

The invention, therefore, also relates to recombinant alpha-interferons in homogeneous pure form which contain less than 20%, preferably less than 5%, more particularly less than 1% methionine interferon, which are free from reduced forms and fragments of alpha-interferon, which contain less than 0.2% oligomer and less than 2% dimer/trimer/tetramer, preferably no oligomers, tetramers, trimers or dimers, and which preferably contain more than 90% of the native monomer and preferably is entirely free from disulfide isomers of native monomeric alpha-interferon.

The invention further relates to the recombinant alpha-interferons of various species described which, when administered to particular species, do not stimulate any antibodies, and also solid interferons.

A recombinant human alpha-interferon with the properties described above, preferably a recombinant human alpha-interferon which has the amino acid sequence:

| Cys | Asp | Leu | Pro | Gln | Thr | His | Ser | Leu | Gly | Ser | Arg |
|---|---|---|---|---|---|---|---|---|---|---|---|
| Arg | Thr | Leu | Met | Leu | Leu | Ala | Gln | Met | Arg | Arg | Ile |
| Ser | Leu | Phe | Ser | Cys | Leu | Lys | Asp | Arg | Arg | Asp | Phe |
| Gly | Phe | Pro | Gln | Glu | Glu | Phe | Gly | Asn | Gln | Phe | Gln |
| Lys | Ala | Glu | Thr | Ile | Pro | Val | Leu | His | Glu | Met | Ile |
| Gln | Gln | Ile | Phe | Asn | Leu | Phe | Ser | Thr | Lys | Asp | Ser |
| Ser | Ala | Ala | Trp | Asp | Glu | Thr | Leu | Leu | Asp | Lys | Phe |
| Tyr | Thr | Glu | Leu | Tyr | Gln | Gln | Leu | Asn | Asp | Leu | Glu |
| Ala | Cys | Val | Ile | Gln | Gly | Val | Gly | Val | Thr | Glu | Thr |
| Pro | Leu | Met | Lys | Glu | Asp | Ser | Ile | Leu | Ala | Val | Arg |
| Lys | Tyr | Phe | Gln | Arg | Ile | Thr | Leu | Tyr | Leu | Lys | Glu |
| Lys | Lys | Tyr | Ser | Pro | Cys | Ala | Trp | Glu | Val | Val | Arg |
| Ala | Glu | Ile | Met | Arg | Ser | Phe | Ser | Leu | Ser | Thr | Asn |
| Leu | Gln | Glu | Ser | Leu | Arg | Ser | Lys | Glu | | | | is preferred.

A recombinant, non-immunogenic, solid human alpha-interferon which corresponds to the amino acid sequence:

| Cys | Asp | Leu | Pro | Gln | Thr | His | Ser | Leu | Gly | Ser |
|---|---|---|---|---|---|---|---|---|---|---|
| Arg | Arg | Thr | Leu | Met | Ley | Leu | Ala | Gln | Met | Arg |
| Arg | Ile | Ser | Leu | Phe | Ser | Cys | Leu | Lys | Asp | Arg |
| Arg | Asp | Phe | Gly | Phe | Pro | Gln | Glu | Glu | Phe | Gly |
| Asn | Gln | Phe | Gln | Lys | Ala | Glu | Thr | Ile | Pro | Val |
| Leu | His | Glu | Met | Ile | Gln | Gln | Ile | Phe | Asn | Leu |
| Phe | Ser | Thr | Lys | Asp | Ser | Ser | Ala | Ala | Trp | Asp |
| Glu | Thr | Leu | Leu | Asp | Lys | Phe | Tyr | Thr | Glu | Leu |
| Tyr | Gln | Gln | Leu | Asn | Asp | Leu | Glu | Ala | Cys | Val |
| Ile | Gln | Gly | Val | Gly | Val | Thr | Glu | Thr | Pro | Leu |
| Met | Lys | Glu | Asp | Ser | Ile | Leu | Ala | Val | Arg | Lys |
| Tyr | Phe | Gln | Arg | Ile | Thr | Leu | Tyr | Leu | Lys | Glu |
| Lys | Lys | Tyr | Ser | Pro | Cys | Ala | Trp | Glu | Val | Val |
| Arg | Ala | Glu | Ile | Met | Arg | Ser | Phe | Ser | Leu | Ser |
| Thr | Asn | Leu | Gln | Glu | Ser | Leu | Arg | Ser | Lys | Glu | and is present in pure homogeneous form containing less than 5% methionine interferon, which is free from reduced forms and fragments of interferon, which contains less than 0.2% oligomer and less than 2% dimer/trimer/tetramer and, wherein more than 95% of the monomer content consists of the native monomeric alpha-interferon with disulfide bridges between the cysteines at positions 1 and 98 and 29 and 138, is particularly preferred.

The process according to the invention makes it possible to remove impurities and interferon contaminants under very mild conditions. This will be explained more fully using the example of the alpha$_2$-Arg interferon which has the amino acid sequence:

| Cys | Asp | Leu | Pro | Gln | Thr | His | Ser | Leu | Gly | Ser |
|---|---|---|---|---|---|---|---|---|---|---|
| Arg | Arg | Thr | Leu | Met | Leu | Leu | Ala | Gln | Met | Arg |
| Arg | Ile | Ser | Leu | Phe | Ser | Cys | Leu | Lys | Asp | Arg |
| Arg | Asp | Phe | Gly | Phe | Pro | Gln | Glu | Glu | Phe | Gly |
| Asn | Gln | Phe | Gln | Lys | Ala | Glu | Thr | Ile | Pro | Val |
| Leu | His | Glu | Met | Ile | Gln | Gln | Ile | Phe | Asn | Leu |
| Phe | Ser | Thr | Lys | Asp | Ser | Ser | Ala | Ala | Trp | Asp |
| Glu | Thr | Leu | Leu | Asp | Lys | Phe | Tyr | Thr | Glu | Leu |
| Tyr | Gln | Gln | Leu | Asn | Asp | Leu | Glu | Ala | Cys | Val |
| Ile | Gln | Gly | Val | Gly | Val | Thr | Glu | Thr | Pro | Leu |
| Met | Lys | Glu | Asp | Ser | Ile | Leu | Ala | Val | Arg | Lys |
| Tyr | Phe | Gln | Arg | Ile | Thr | Leu | Tyr | Leu | Lys | Glu |
| Lys | Lys | Tyr | Ser | Pro | Cys | Ala | Trp | Glu | Val | Val |
| Arg | Ala | Glu | Ile | Met | Arg | Ser | Phe | Ser | Leu | Ser |
| Thr | Asn | Leu | Gln | Glu | Ser | Leu | Arg | Ser | Lys | Glu | but other alpha-interferons may also be prepared and purified using the process according to the invention, if necessary with slight non-inventive modifications.

The acid-precipitated deep frozen biomass is thawed by stirring in 1% acetic acid. This and all subsequent operations are carried out at low temperatures, typically about 5° C.

The protein is extracted from the cells, typically as described in detail in Patent Application DE 34 32 196.9, by breaking up the bacterial cells in a homogenizer, adding a precipitation adjuvant such as polyethyleneimine PEI-600 in a concentration ranging from 0.1 to 0.25%, adjusting the pH to 7.5–10.0 with the aid of NaOH and stirring the suspension for several hours.

The pH is then adjusted to 7.5, the crude extract is clarified under mild conditions and samples are taken for determining the protein and for the interferon test.

In spite of the known vulnerability of polypeptides such as interferon to the shearing forces which occur under mechanical influences (*Proc. Soc. Exp. Biol. Med.* 146: 249-253 (1974)) surprisingly high yields of crude interferon are achieved using this process under these pH conditions.

Examination of different fermentation batches showed that the composition of the mixture varied as a function of the fermentation conditions. In particular, the proportion of component 1, namely, methionine alpha-interferon, which is a very difficult component to remove, varied with the duration of fermentation; methionine alpha-interferon was only formed after 8-9 hours of fermentation. By stopping fermentation in good time, therefore, it is possible to obtain interferon preparations which contain no methionine-interferon.

Solid ammonium sulphate is added to the clarified crude solution up to 65% of saturation. After all the ammonium sulphate has dissolved, the mixture is kept cool overnight, and the precipitate that forms is separated off and stored at low temperatures, typically $-20°$ C., until required.

Samples for the interferon test are taken from the clear supernatant in order to monitor the precipitation of the interferon. No more than 5% of the interferon should remain in the supernatant.

The ammonium sulphate pellet is dissolved in a salt solution, typically in 0.01M NaCl, the pH is adjusted to about 7.5 with base such as NaOH and the solution is stirred, e.g., for 2 hours. The insoluble fraction is removed and possibly extracted once more with, e.g., 0.01M NaCl.

The combined clear solutions are dialyzed using a sterile, pyrogen-free dialysis cartridge. The osmolarity of the interferon solution should be about 390-430 mOsmol/l after running through two to three times. Aliquots for the interferon test may be taken from the clarified solution.

"Tandem Chromatography" is used for the further purification: a combination of a cellulose preliminary column and subsequent affinity chromatography with highly specific monoclonal antibodies. The preliminary column, an ion exchanger column, is used to keep any difficultly soluble sample constituents away from the antibody column. For the preliminary column, DE-52 cellulose (Whatman) is stirred thoroughly with Tris/NaCl buffer, pH about 7.5, and introduced into a chromatography column. The adsorbent is washed with buffer until the eluate shows no further changes in pH and osmolarity. For the preliminary column, 0.5-1.0 g of DE 52 cellulose in about 0.025M Tris/HCl+0.2M NaCl are used per gram of biomass; it is freshly prepared for each purification.

For the antibody column, purified monoclonal anti-interferon-IgG obtained from mouse ascites fluid is coupled to BrCN-activated Sepharose 4B (Pharmacia) as the carrier. The finished column material is stored cold in phosphate-buffered saline solution (PBS) with sodium azide as a preservative. Before being used for the first time or after a lengthy storage period, the antibody column is washed with 0.1M citric acid in 25% ethylene glycol in order to eliminate any soluble components, and then washed with PBS until neutral. A column volume of from 0.2-1.0 ml is required for each gram of biomass in the antibody column; this column may be used several times. The dialyzed interferon solution is first pumped through both columns (preliminary column and antibody column) and the eluate is monitored by measuring the extinction at 280 nm. After the interferon solution had been applied, it is washed with Tris/NaCl buffer, pH 7.5, until the quantity of protein in the eluate has fallen to about 1/20th of the plateau value. In order to check that the interferon has bound to the antibody column, the eluate is tested for its interferon content. The antibody column is then separated from the preliminary column and washed on its own with Tris/NaCl buffer, pH about 7.5, until no further protein could be detected in the eluate.

Elution of the interferon bound to the antibody is carried out using 0.1M citric acid in 25% ethylene glycol, and the extinction of the eluate at 280 nm is monitored. The protein peak containing the interferon is collected. The interferon pool is stored, typically at $-20°$ C., until final purification. An interferon test, protein determination and reverse phase HPLC analysis show that 60-90% pure IFN-alpha is obtained after this purification. In addition to oligomeric forms, this interferon pool contained reduced forms with free sulfhydryl groups, dimers, trimers, tetramers and the non-native monomer. These components are all biologically and immunologically characterizable as IFN. Surprisingly, some of these components may be removed by isoelectric precipitation at pH about 4.5 (with ammonia). The fractions of the components with reduced disulfide bridges, i.e., the forms with free sulfhydryl groups (components 5 and 6), in particular, are thus reduced. Analysis of the precipitate shows that only small amounts of the monomeric interferon are carried down.

Final purification is carried out using an FPLC apparatus such as with a MONO-S column, Type HR 10/10 (cation exchanger), which may be charged with up to 60 mg of protein. This column material constitutes a high performance ion exchanger with an exceptional separating action and the great advantage that final purification takes only a few hours, in spite of the relatively large quantity of protein to be purified; the buffer solutions may be used after being filtered sterile, and the work may be done at ambient temperature.

The clear supernatant obtained after isoelectric precipitation is applied to the column. The buffer used in the FPLC separation is particularly important. It has to be capable of eluting the interferon components so that they may be clearly distinguished and then it has to be completely removable. The ammonium acetate buffer with which the interferon is eluted through a series of gradients has these properties. Interferon is eluted as a sharp peak with a weak shoulder. Both the "shoulder" fraction (K3) and also the fractions eluted subsequently (K5-K7) are separated from the main peak of the pure interferon. The peak of pure interferon is collected, and aliquots are taken from it for HPLC analysis, SDS gel electrophoresis, protein determination, interferon testing, and endotoxin determination.

By this chromatography, virtually all the components are separated from the main peak, and homogeneous interferon is obtained showing a monomer content of over 99% in gel permeation HPLC. Reverse phase HPLC shows only about 1% of non-native monomer and chromatofocusing shows about 2.5% of non-native monomer.

The MONO-S column is washed before re-use with 0.5M NaCl+0.1M Na-phosphate, pH 8.0, in order to eliminate any adsorbed impurities; it is stored in 25% ethanol.

The volatile buffer may be totally removed by lyophilization. For this, the IFN pool is transferred into autoclaved lyo-ampoules (capacity 8 ml) in batches of not more than 2 ml; this corresponds to a quantity from 1 to about 8 mg of pure interferon per ampoule. The ampoules are then sealed with prewashed and autoclaved lyo-stoppers and cooled to at least −20° C. Lyophilization is carried out at −10° C. under a vacuum of less than 1 torr. After removal of the buffer solution, the temperature is increased at 25° C. and lyophilization is continued for at least 1 hour. The vacuum is released and the stoppers are immediately sealed in place. After being sealed with aluminum closures, the ampoules are then stored in the refrigerator or at −20° C.

As has been shown, careful monitoring of fermentation (relatively early harvesting), together with the process according to the invention, has made it possible for the first time to prepare an alpha-interferon which not only has a degree of purity of over 98% with regard to its interferon content but also consists of more than 95% native monomeric alpha-interferon with regard to its homogeneity based on the various interferon components.

This high degree of purity and homogeneity has also made it possible for the first time to obtain interferon in solid form free from salts and buffer constituents. It is therefore possible for the first time to store alpha-interferon for months without the use of stabilizers; this has significant advantages in terms of storage, dispatch and, not least, galenic developments, over the inteferons which have hitherto always been stabilized with albumin. Even after 11 months' storage at 4° C., no loss of contents could be detected.

The crystalline human leukocyte interferon described in EPA 83 734 consists of crystals of polyethylene glycol as the precipitating agent with interferon, but not a pure, homogeneous and crystalline interferon as the title would have one believe.

The alpha-interferon prepared according to the invention was, as is already known, dissolved by the addition of human serum albumin, filtered until sterile and transferred into vials under aseptic conditions, in suitable concentrations depending on the molecular application.

In clinical trials, the alpha-interferon prepared according to the invention proved to be non-immunogenic and exceptionally well tolerated. In all, up to January 1985, 75 patients have been treated with the non-immunogenic alpha-interferon: 58 patients with tumor indications and 17 with viral indications. Antibodies were stimulated in no patients throughout the therapy, the period of treatment being 15 or more weeks in some cases and up to 35 weeks.

The process according to the invention has made it possible for the first time to prepare a highly pure alpha$_2$-interferon which is homogeneous in terms of the native monomeric interferon, solid, free from salts and buffer constituents and non-immunogenic.

Amino acid sequence analysis by known methods yielded the following amino acid sequence:

| Cys | Asp | Leu | Pro | Gln | Thr | His | Ser | Leu | Gly | Ser | Arg |
|-----|-----|-----|-----|-----|-----|-----|-----|-----|-----|-----|-----|
| Arg | Thr | Leu | Met | Leu | Leu | Ala | Gln | Met | Arg | Arg | Ile |
| Ser | Leu | Phe | Ser | Cys | Leu | Lys | Asp | Arg | Arg | Asp | Phe |
| Gly | Phe | Pro | Gln | Glu | Glu | Phe | Gly | Asn | Gln | Phe | Gln |
| Lys | Ala | Glu | Thr | Ile | Pro | Val | Leu | His | Glu | Met | Ile |
| Gln | Gln | Ile | Phe | Asn | Leu | Phe | Ser | Thr | Lys | Asp | Ser |
| Ser | Ala | Ala | Trp | Asp | Glu | thr | Leu | Leu | Asp | Lys | Phe |
| Tyr | Thr | Glu | Leu | Tyr | Gln | Gln | Leu | Asn | Asp | Leu | Glu |
| Ala | Cys | Val | Ile | Gln | Gly | Val | Gly | Val | Thr | Glu | Thr |
| Pro | Leu | Met | Lys | Glu | Asp | Ser | Ile | Leu | Ala | Val | Arg |
| Lys | Tyr | Phe | Gln | Arg | Ile | Thr | Leu | Tyr | Leu | Lys | Glu |
| Lys | Lys | Tyr | Ser | Pro | Cys | Ala | Trp | Glu | Val | Val | Ag |
| Ala | Glu | Ile | Met | Arg | Ser | Phe | Ser | Leu | Ser | Thr | Asn |
| Leu | Gln | Glu | Ser | Leu | Arg | Ser | Lys | Glu |     |     |     |

With regard to the fermentation mixture, in particular, the process according to the invention can be used without restriction, within wide limits. Thus, it is also possible to use biomasses of other host organisms which give comparable IFN yields after mechanical disruption, and interferons which react in a similarly specific manner with the EBI-1 monoclonal antibody, e.g., IFN-alpha$_1$. Other interferons with a lesser homology to alpha interferon may also be purified using the method according to the invention if a corresponding highly specific monoclonal antibody is used.

The invention relates specifically to processes for the preparation of recombinant alpha-interferon, characterized in that the host organism containing the interferon gene is cultivated under conventional conditions, after the conventional growth period the cells are killed off and harvested, the expressed interferon is removed in a conventional manner, the cell debris is removed in a slightly alkaline medium, the interferon is concentrated and subjected to preliminary purification by Tandem Chromatography, the eluate is adjusted to pH 4.0–4.8 to remove any impurities, and the interferon is finally purified by chromatography on a cation exchanger column with a volatile buffer as eluant, and is then lyophilized. When the host organism is E. coli, in the preferred embodiment the cells are killed off after a growth period in which not more than 20%, preferably not more than 5%, and more particularly not more than 1% methionine interferon is formed; the cells are disrupted in a homogenizer at pH 2 and the interferon is extracted.

In the preferred embodiment, Tandem Chromatography is used to remove contaminants from a pure alpha-interferon. This consists of a preliminary cellulose column and an affinity chromatography column. The substance to be purified is washed through both columns with a suitable washing solution, and the alpha-interferon is subsequently eluted from the affinity column with a suitable eluant. The preliminary column is charged with DE-52 cellulose and the affinity column is charged with a monoclonal anti-interferon IgG antibody coupled to a carrier. The substance to be purified is washed through both columns with a Tris-NaCl buffer, pH 7.5, and the alpha-interferon is subsequently eluted from the affinity column with 0.1M citric acid in 25% ethylene glycol. The monoclonal antibody used is EBI 1.

The eluate from the Tandem Chromatography is adjusted to pH 4.5 to remove any impurities by isoelectric precipitation, and a MONO-S, Type HR 10/10 cation exchanger is used for the final purification. A linear concentration gradient prepared from 0.1–1.0M, preferably 0.1–0.5M ammonium acetate buffer at pH values of 4.5 is used.

In the preferred embodiments, the process produces a homogeneous, pure, human recombinant alpha-interferon with the amino acid sequence

| Cys | Asp | Leu | Pro | Gln | Thr | His | Ser | Leu | Gly | Ser |
|-----|-----|-----|-----|-----|-----|-----|-----|-----|-----|-----|
| Arg | Arg | Thr | Leu | Met | Leu | Leu | Ala | Gln | Met | Arg |
| Arg | Ile | Ser | Leu | Phe | Ser | Cys | Leu | Lys | Asp | Arg |
| Arg | Asp | Phe | Gly | Phe | Pro | Gln | Glu | Glu | Phe | Gly |
| Asn | Gln | Phe | Gln | Lys | Ala | Glu | Thr | Ile | Pro | Val |
| Leu | His | Glu | Met | Ile | Gln | Gln | Ile | Phe | Asn | Leu |
| Phe | Ser | Thr | Lys | Asp | Ser | Ser | Ala | Ala | Trp | Asp |
| Glu | Thr | Leu | Leu | Asp | Lys | Phe | Tyr | Thr | Glu | Leu |
| Tyr | Gln | Gln | Leu | Asn | Asp | Leu | Glu | Ala | Cys | Val |
| Ile | Gln | Gly | Val | Gly | Val | Thr | Glu | Thr | Pro | Leu |
| Met | Lys | Glu | Asp | Ser | Ile | Leu | Ala | Val | Arg | Lys |
| Tyr | Phe | Gln | Arg | Ile | Thr | Leu | Tyr | Leu | Lys | Glu |
| Lys | Lys | Tyr | Ser | Pro | Cys | Ala | Trp | Glu | Val | Val |
| Arg | Ala | Glu | Ile | Met | Arg | Ser | Phe | Ser | Leu | Ser |
| Thr | Asn | Leu | Gln | Glu | Ser | Leu | Arg | Ser | Lys | Glu | and which contains less than 5% methionine-interferon, which is free from reduced forms and fragments of alpha-interferon, which contains less than 0.2% oligomer and less than 2% dimer/trimer/tetramer, and wherein the native monomeric alpha-interferon contains disulfide bridges between the cysteines at positions 1 and 98 and 29 and 138.

The invention further describes recombinant alpha-interferons which may be prepared in accordance to the invention, characterized in that they are obtained in homogeneous pure form with less than 20%, preferably less than 5%, more particularly less than 1% methionine-interferon; each is produced in homogeneous pure form, free from reduced forms and fragments and containing less than 0.2% oligomer and 2% dimer/trimer/tetramer; each can be prepared free from oligomers and dimers/trimers/tetramers; wherein over 90% of the monomer content is native monomeric alpha-interferon or is free from non-native monomeric interferon; characterized in that it does not stimulate any antibodies; and characterized in that it occurs in solid form.

In the preferred embodiment, human alpha-interferon is produced according to the invention which corresponds to the amino acid sequence,

| Cys | Asp | Leu | Pro | Gln | Thr | His | Ser | Leu | Gly | Ser |
|-----|-----|-----|-----|-----|-----|-----|-----|-----|-----|-----|
| Arg | Arg | Thr | Leu | Met | Leu | Leu | Ala | Gln | Met | Arg |
| Arg | Ile | Ser | Leu | Phe | Ser | Cys | Leu | Lys | Asp | Arg |
| Arg | Asp | Phe | Gly | Phe | Pro | Gln | Glu | Glu | Phe | Gly |
| Asn | Gln | Phe | Gln | Lys | Ala | Glu | Thr | Ile | Pro | Val |
| Leu | His | Glu | Met | Ile | Gln | Gln | Ile | Phe | Asn | Leu |
| Phe | Ser | Thr | Lys | Asp | Ser | Ser | Ala | Ala | Trp | Asp |
| Glu | Thr | Leu | Leu | Asp | Lys | Phe | Tyr | Thr | Glu | Leu |
| Tyr | Gln | Gln | Leu | Asn | Asp | Leu | Glu | Ala | Cys | Val |
| Ile | Gln | Gly | Val | Gly | Val | Thr | Glu | Thr | Pro | Leu |
| Met | Lys | Glu | Asp | Ser | Ile | Leu | Ala | Val | Arg | Lys |
| Tyr | Phe | Gln | Arg | Ile | Thr | Leu | Tyr | Leu | Lys | Glu |
| Lys | Lys | Tyr | Ser | Pro | Cys | Ala | Trp | Glu | Val | Val |
| Arg | Ala | Glu | Ile | Met | Arg | Ser | Phe | Ser | Leu | Ser |
| Thr | Asn | Leu | Gln | Glu | Ser | Leu | Arg | Ser | Lys | Glu |

Recombinant human alpha-interferon, which corresponds to the amino acid sequence,

| Cys | Asp | Leu | Pro | Gln | Thr | His | Ser | Leu | Gly | Ser |
|-----|-----|-----|-----|-----|-----|-----|-----|-----|-----|-----|
| Arg | Arg | Thr | Leu | Met | Ley | Leu | Ala | Gln | Met | Arg |
| Arg | Ile | Ser | Leu | Phe | Ser | Cys | Leu | Lys | Asp | Arg |
| Arg | Asp | Phe | Gly | Phe | Pro | Gln | Glu | Glu | Phe | Gly |
| Asn | Gln | Phe | Gln | Lys | Ala | Glu | Thr | Ile | Pro | Val |
| Leu | His | Glu | Met | Ile | Gln | Gln | Ile | Phe | Asn | Leu |
| Phe | Ser | Thr | Lys | Asp | Ser | Ser | Ala | Ala | Trp | Asp |
| Glu | Thr | Leu | Leu | Asp | Lys | Phe | Tyr | Thr | Glu | Leu |
| Tyr | Gln | Gln | Leu | Asn | Asp | Leu | Glu | Ala | Cys | Val |
| Ile | Gln | Gly | Val | Gly | Val | Thr | Glu | Thr | Pro | Leu |
| Met | Lys | Glu | Asp | Ser | Ile | Leu | Ala | Val | Arg | Lys |
| Tyr | Phe | Gln | Arg | Ile | Thr | Leu | Tyr | Leu | Lys | Glu |
| Lys | Lys | Tyr | Ser | Pro | Cys | Ala | Trp | Glu | Val | Val |
| Arg | Ala | Glu | Ile | Met | Arg | Ser | Phe | Ser | Leu | Ser |
| Thr | Asn | Leu | Gln | Glu | Ser | Leu | Arg | Ser | Lys | Glu | is present in homogeneous pure form, with less than 5% methionine interferon, less than 0.2% oligomers and less than 2% dimers/trimers/tetramers, free from reduced forms and fragments of alpha-interferon, over 90% of the monomer content consisting of the native monomeric alpha-interferon with disulfide bridges between the cysteines at positions 1 and 98 and 29 and 138.

In the preferred embodiments, alpha-interferon according to the invention is used for the therapeutic treatment of viral diseases and tumors. The pharmaceutical preparation for therapeutic treatment is characterized in that it contains an alpha-interferon according to the invention and one or more inert pharmaceutical excipients and/or carriers.

In the preferred embodiment, the process of the invention prepares a solid alpha-interferon, and the alpha-interferon is non-immunogenic.

In the preferred embodiment, the process is characterized in that the host organism contains the gene coding for human alpha-interferon with the amino acid sequence

| Cys | Asp | Leu | Pro | Gln | Thr | His | Ser | Leu | Gly | Ser |
|-----|-----|-----|-----|-----|-----|-----|-----|-----|-----|-----|
| Arg | Arg | Thr | Leu | Met | Leu | Leu | Ala | Gln | Met | Arg |
| Arg | Ile | Ser | Leu | Phe | Ser | Cys | Leu | Lys | Asp | Arg |
| Arg | Asp | Phe | Gly | Phe | Pro | Gln | Glu | Glu | Phe | Gly |
| Asn | Gln | Phe | Gln | Lys | Ala | Glu | Thr | Ile | Pro | Val |
| Leu | His | Glu | Met | Ile | Gln | Gln | Ile | Phe | Asn | Leu |
| Phe | Ser | Thr | Lys | Asp | Ser | Ser | Ala | Ala | Trp | Asp |
| Glu | Thr | Leu | Leu | Asp | Lys | Phe | Tyr | Thr | Glu | Leu |
| Tyr | Gln | Gln | Leu | Asn | Asp | Leu | Glu | Ala | Cys | Val |
| Ile | Gln | Gly | Val | Gly | Val | Thr | Glu | Thr | Pro | Leu |
| Met | Lys | Glu | Asp | Ser | Ile | Leu | Ala | Val | Arg | Lys |
| Tyr | Phe | Gln | Arg | Ile | Thr | Leu | Tyr | Leu | Lys | Glu |
| Lys | Lys | Tyr | Ser | Pro | Cys | Ala | Trp | Glu | Val | Val |
| Arg | Ala | Glu | Ile | Met | Art | Ser | Phe | Ser | Leu | Ser |
| Thr | Asn | Leu | Gln | Glu | Ser | Leu | Arg | Ser | Lys | Glu |

The following examples are intended to illustrate the invention without restricting it in any way.

EXAMPLES

EXAMPLE 1

Mixture E. coli; IFN-alpha$_2$Arg; 28° C.

a) 251 g of acid-precipitated biomass which had been stored at $-20°$ C. were taken up in 2500 ml of 1% acetic acid, stirred for half an hour in an ice bath and homogenized twice for 1 minute using the Ultraturax Type 45/6. Polymin P was added to give a final concentration of 0.25%, the pH was adjusted to 10.0 using 5N NaOH, and the mixture was stirred for 2 hours over an ice bath, and finally the pH was adjusted to 7.50 using 5N HCl.

Centrifuging for 1 hour in a Christ Cryofuge 6-6S at 4° C. and 3000 rpm yielded a clear crude extract of 2540 ml with an interferon content of $17.1 \times 10^9$ I.U. (=100%) and a protein content of 5330 mg, from which a specific activity of $3.21 \times 10^6$ I.U./mg of protein can be calculated.

b) Ammonium sulphate was added until 65% of saturation was reached (430 g/liter of extract). The mixture was stored overnight at 4°-8° C. and the precipitate formed was removed by centrifuging in a Beckmann J 2-21 high speed centrifuge, Rotor JA 10 at 4° C., 10,000 rpm, within 1 hour. The clear supernatant, 3120 ml, contained 0.7% of the interferon contained in the crude extract ($120 \times 10^6$ I.U.).

The pellet was taken up in 0.01M NaCl and stirred for 2 hours at 4°-8° C. The pH was adjusted to 7.50 using 5N NaOH, and the solution was clarified by centrifuging as described above. The clear solution was dialyzed against 0.01M NaCl using a dialysis cartridge (Nephross Allegro, Organon Technika) to give 390 mOsmol/l. The interferon content was $13.3 \times 10^9$ I.U. (=77.6%)

c) The dialyzed material was then chromatographed (Tandem Chromatography). For the preliminary column, 125 g of DE 52 cellulose powder made by Whatman was used in Tris/NaCl buffer, pH 7.5 (0.025M Tris/HCl+0.2M NaCl); this corresponded to 0.5 g of column material per gram of biomass. For the affinity column, monoclonal anti-interferon IgG (EBI 1) coupled to BrCN-activated Sepharose 4B (Pharmacia) was used. The finished column material was stored in phosphate-buffered saline solution (PBS) with sodium azide at 4°-8° C. Before use, the antibody column was washed with 0.1M citric acid in 25% ethylene glycol and then rinsed with PBS until neutral. A column volume of from 0.2 to 1.0 ml was required for each gram of biomass in the antibody column. The dialyzed interferon solution was first pumped through both columns (preliminary cellulose column and antibody column) and the eluate was monitored by measuring the extinction at 280 nm. After the interferon solution had been applied, it was washed with Tris/NaCl buffer, pH 7.5, until the quantity of protein in the eluate had fallen to 1/20th of the plateau value. The antibody column was then separated from the preliminary column and washed on its own with Tris/NaCl buffer, pH 7.5, until no further protein could be detected.

Figure 2:
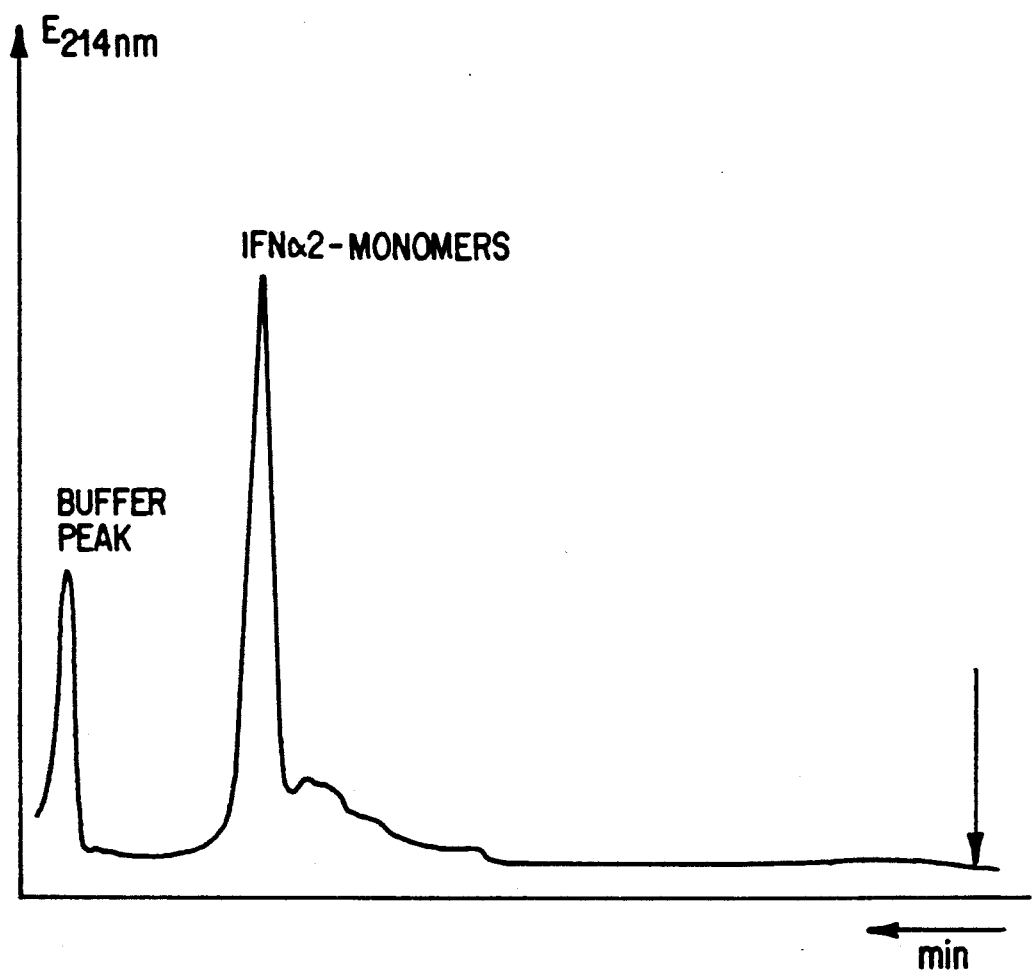
FIG. 2 is a chromatograph of gel permeation HPLC of the acid eluate after Tandem Chromatography. IFN alpha$_2$-monomers are in the main protein peak.
Figure 3:
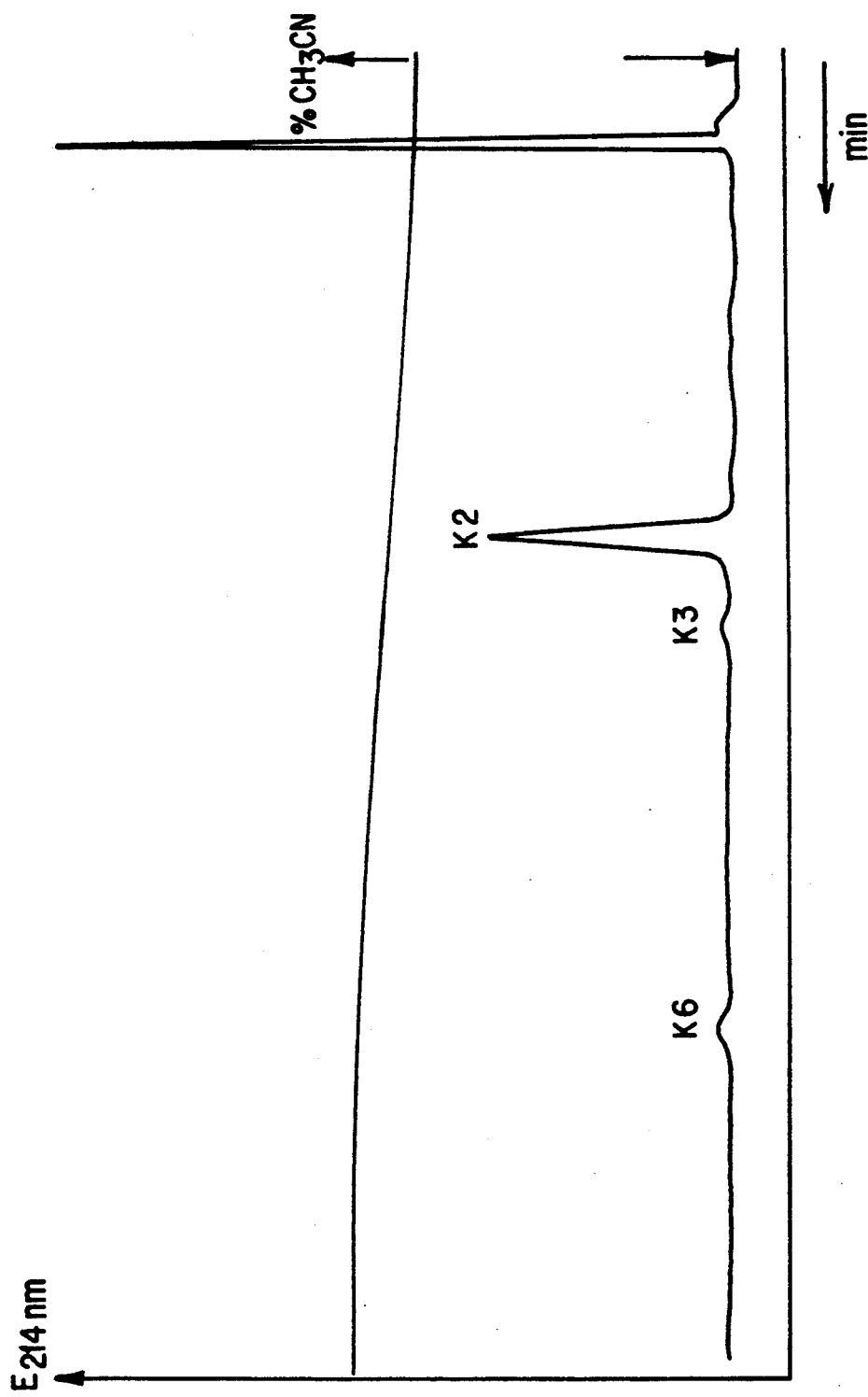
FIG. 3 is a chromatograph of reverse phase HPLC after precipitation at pH 4.5. Only components K1, K2, K3 and K6 are present.
Figure 4:
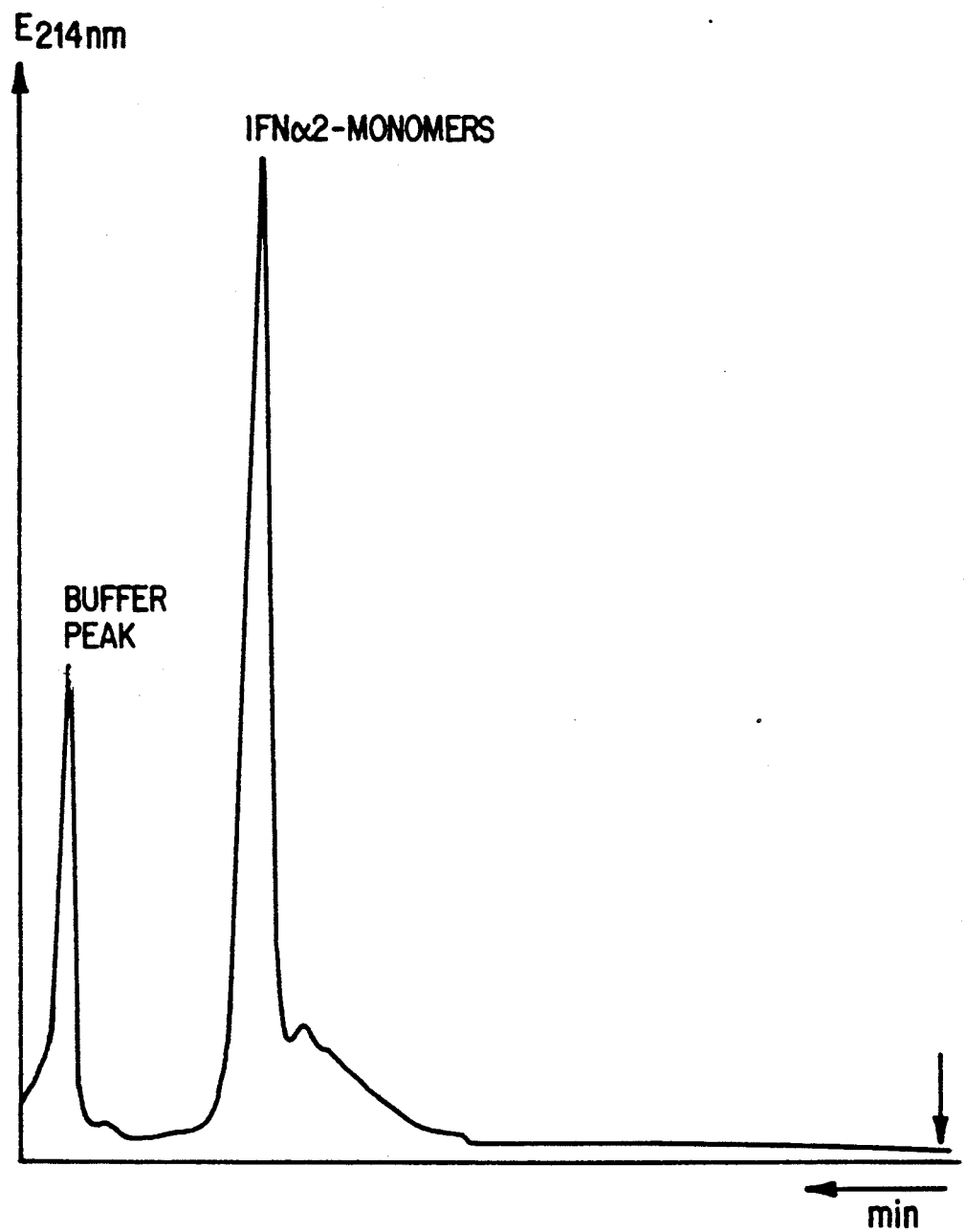
FIG. 4 is a chromatograph of the gel permeation HPLC after precipitation at pH 4.5. The major peak is IFN alpha$_2$-monomer.
Figure 5:
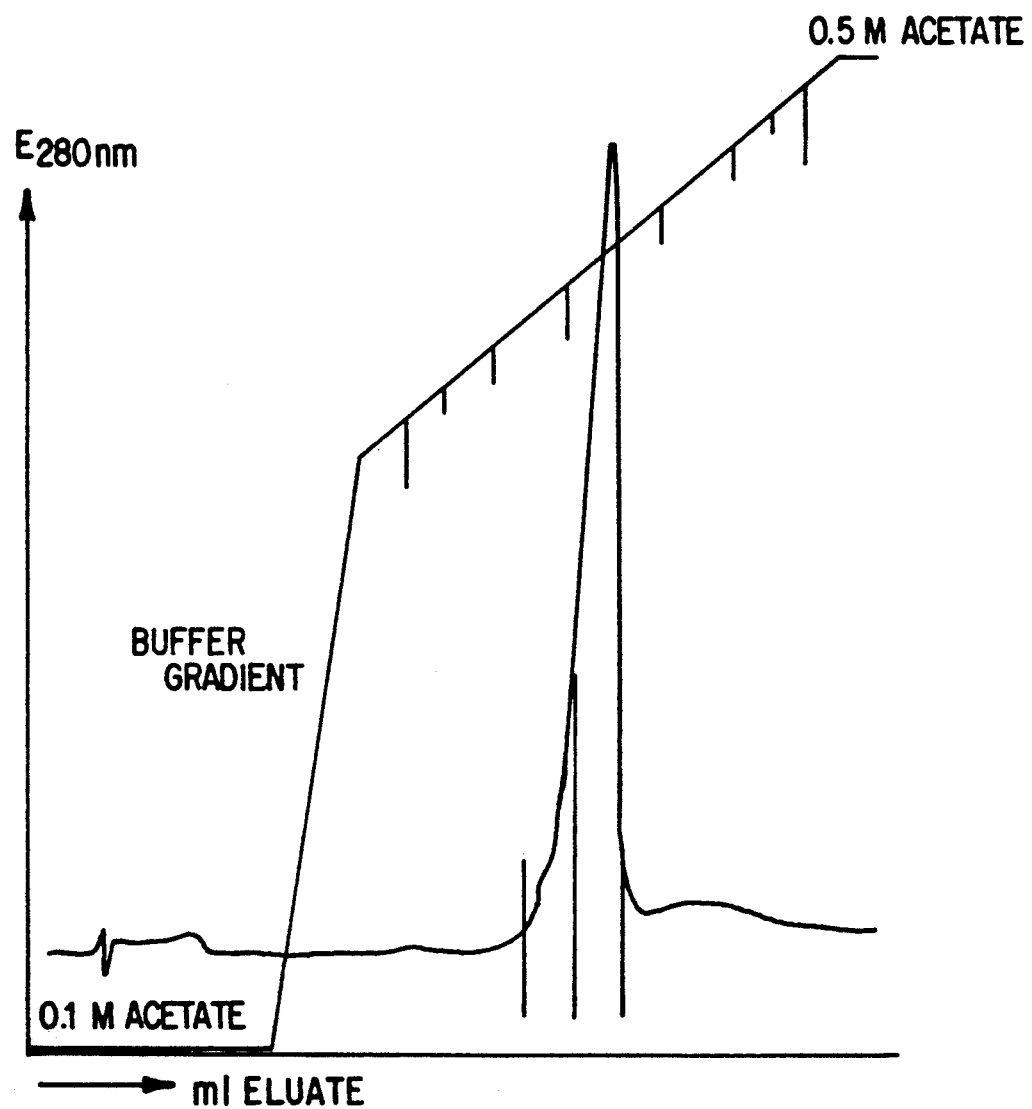
FIG. 5 shows a chromatograph of the FPLC on MONO-S at pH 4.5 with an ammonium acetate gradient from 0.1–0.5M. A single major protein peak as obtained.

Elution of the interferon bound to the antibody was carried out using 0.1M citric acid in 25% ethylene glycol, and again extinction of the eluate at 280 nm was monitored. The protein peak containing the interferon was collected. Eluate (16.8 ml) was obtained with an interferon content of $12.3 \times 10^9$ I.U. (=71.9%) (FIGS. 1 and 2). The total quantity of protein was 54.4 mg, from which a specific activity of $226 \times 10^6$ I.U./mg of protein can be calculated.

d) For further purification, the eluate was adjusted to pH 4.5 with ammonia and the precipitate formed was removed. The clear supernatant (18.3 ml) contained 46.3 mg of protein and had an interferon content of $11.8 \times 10^9$ I.U. based on the crude protein (FIGS. 3 and 4). This corresponded to a yield of 69% ($255 \times 10^6$ I.U./mg of protein).

e) Final purification was carried out with an FPLC apparatus made by Pharmacia with a MONO-S column, Type HR 10/10 (cation exchanger).

Figure 6:
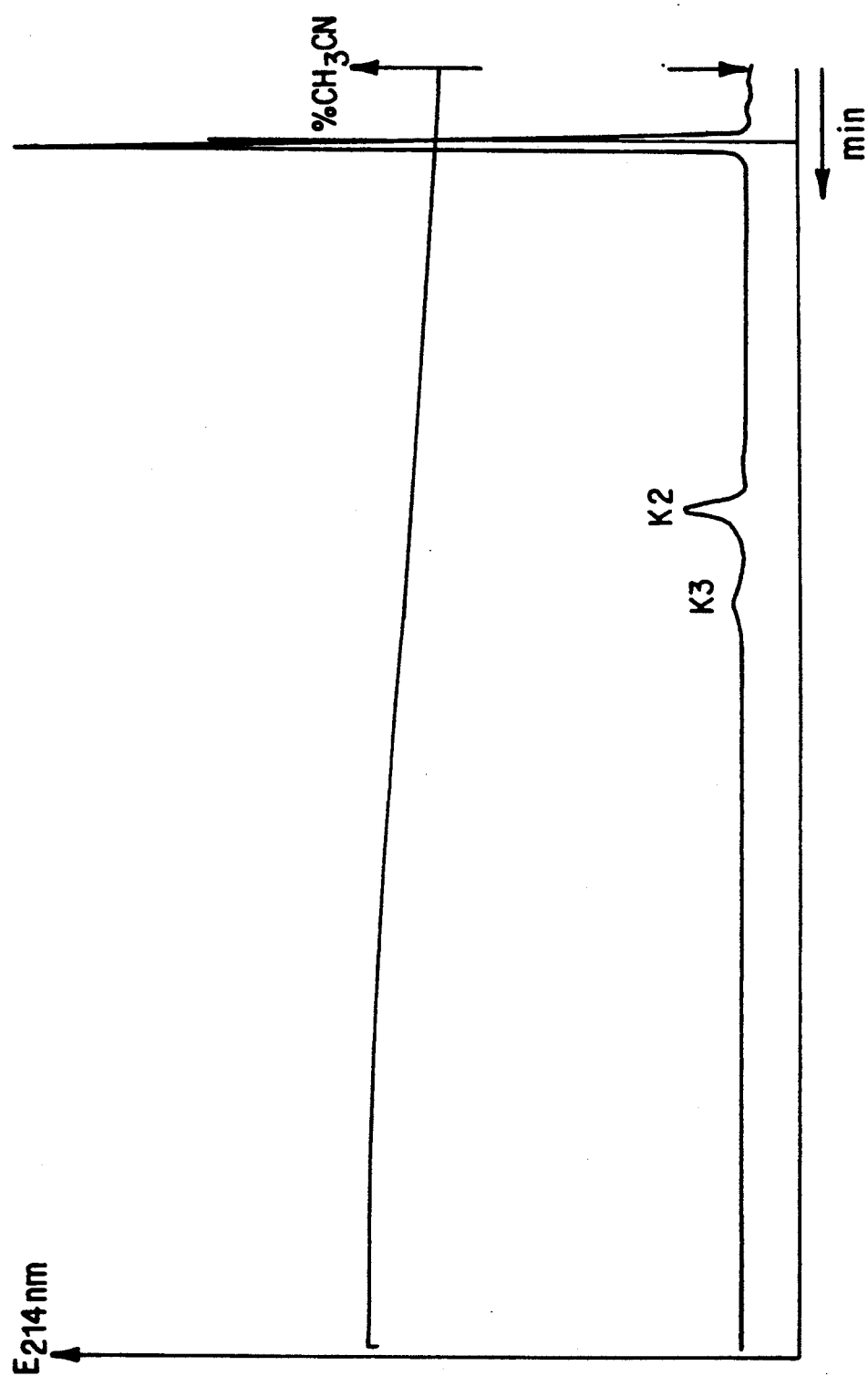
FIG. 6 is a chromatograph of reverse phase HPLC of the "shoulder fraction" of the MONO S-peak, showing components K1, K2 and K3.
Figure 7:
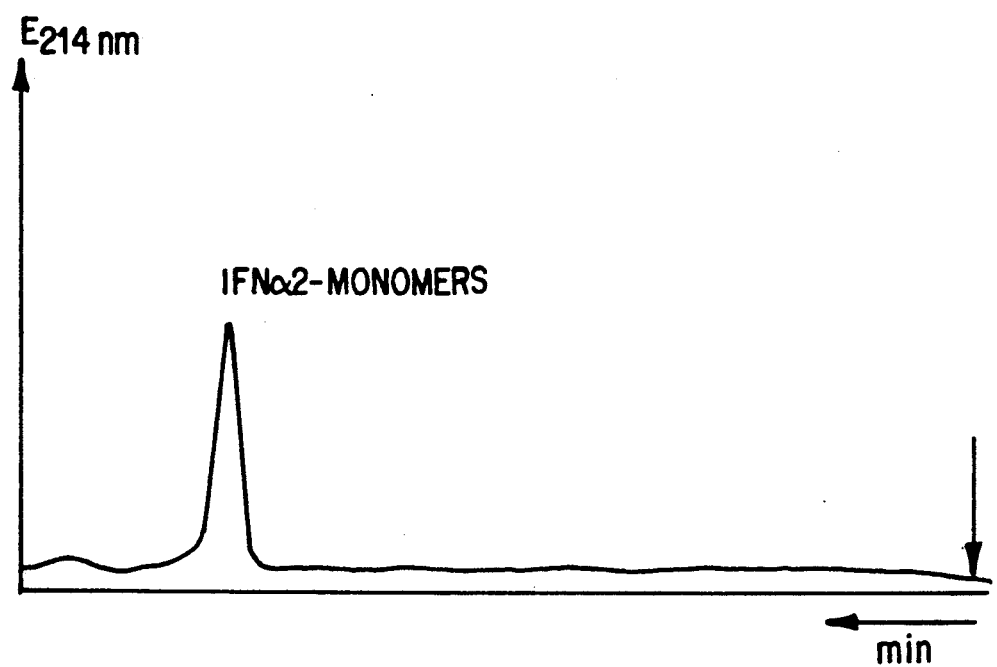
FIG. 7 is a chromatograph of the gel permeation HPLC of the "shoulder fraction" of the MONO S-peak. IFN alpha$_2$-monomers are in the single peak.
Figure 8:
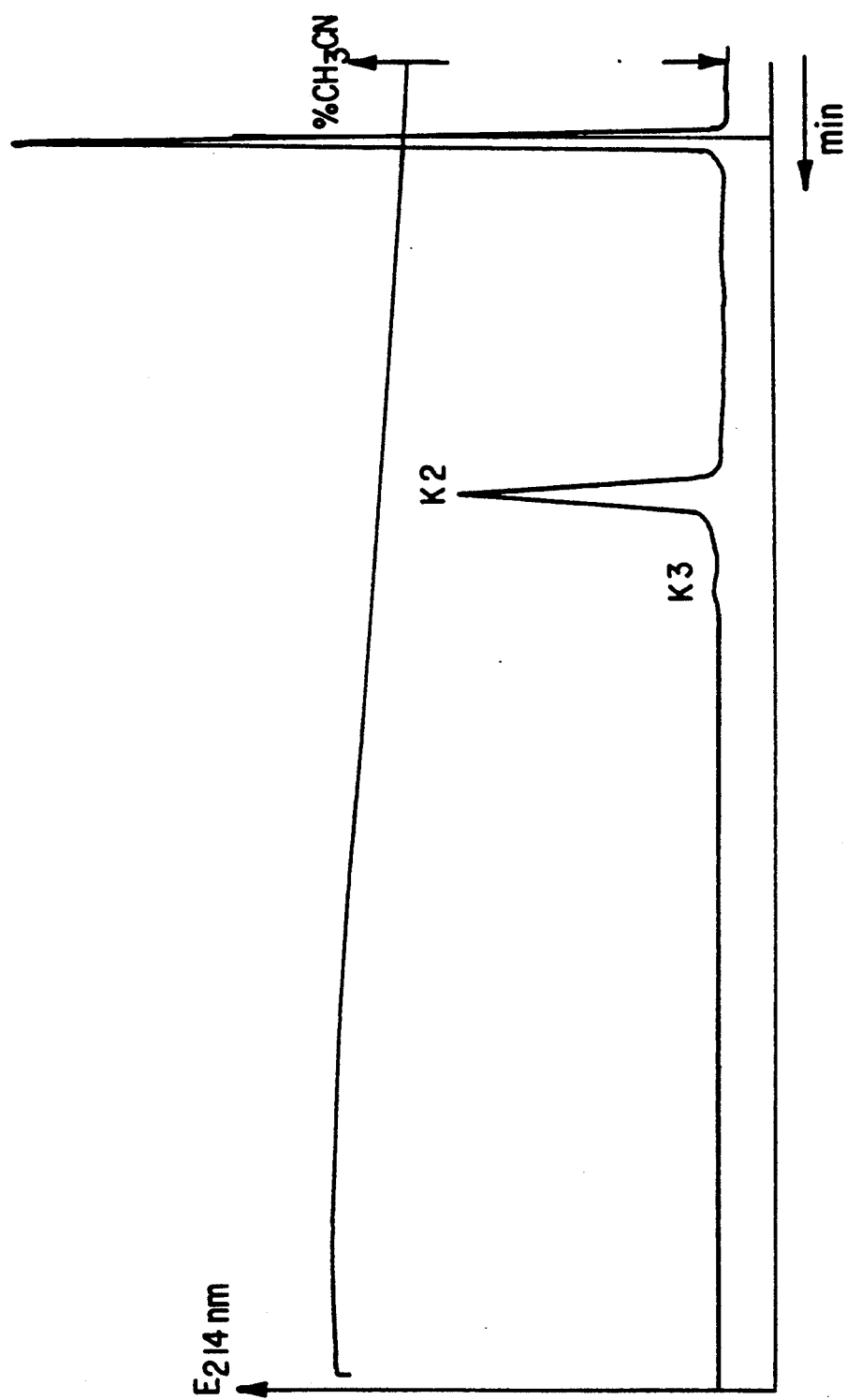
FIG. 8 is a chromatograph of reverse phase HPLC of the "main fraction" of the MONO S-peak. Only K1, K2 and K3 are present.
Figure 9:
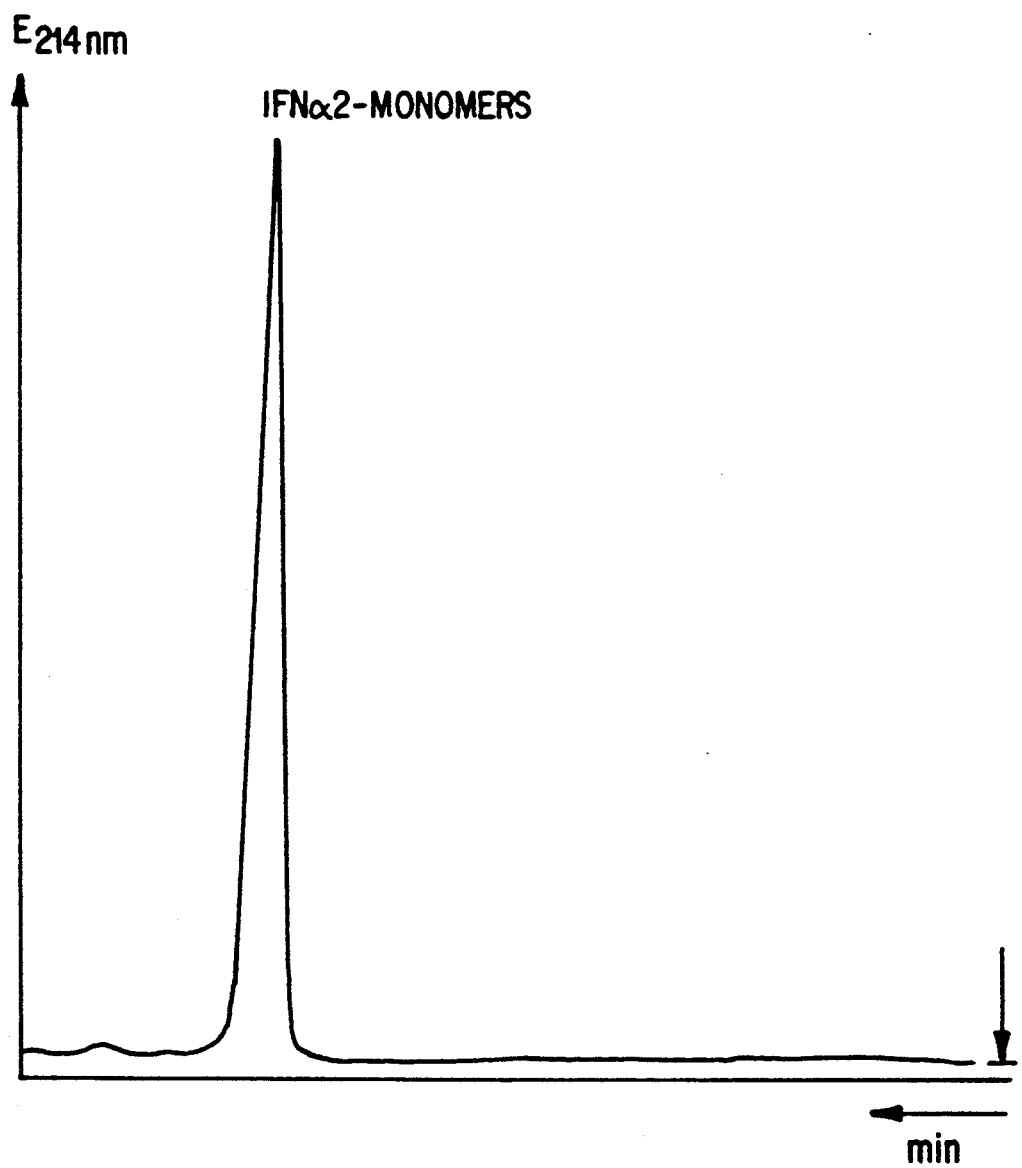
FIG. 9 is a chromatograph of the gel permeation HPLC of the "main fraction" of the MONO S-peak. Only IFN alpha$_2$-monomers are seen.
Figure 10:
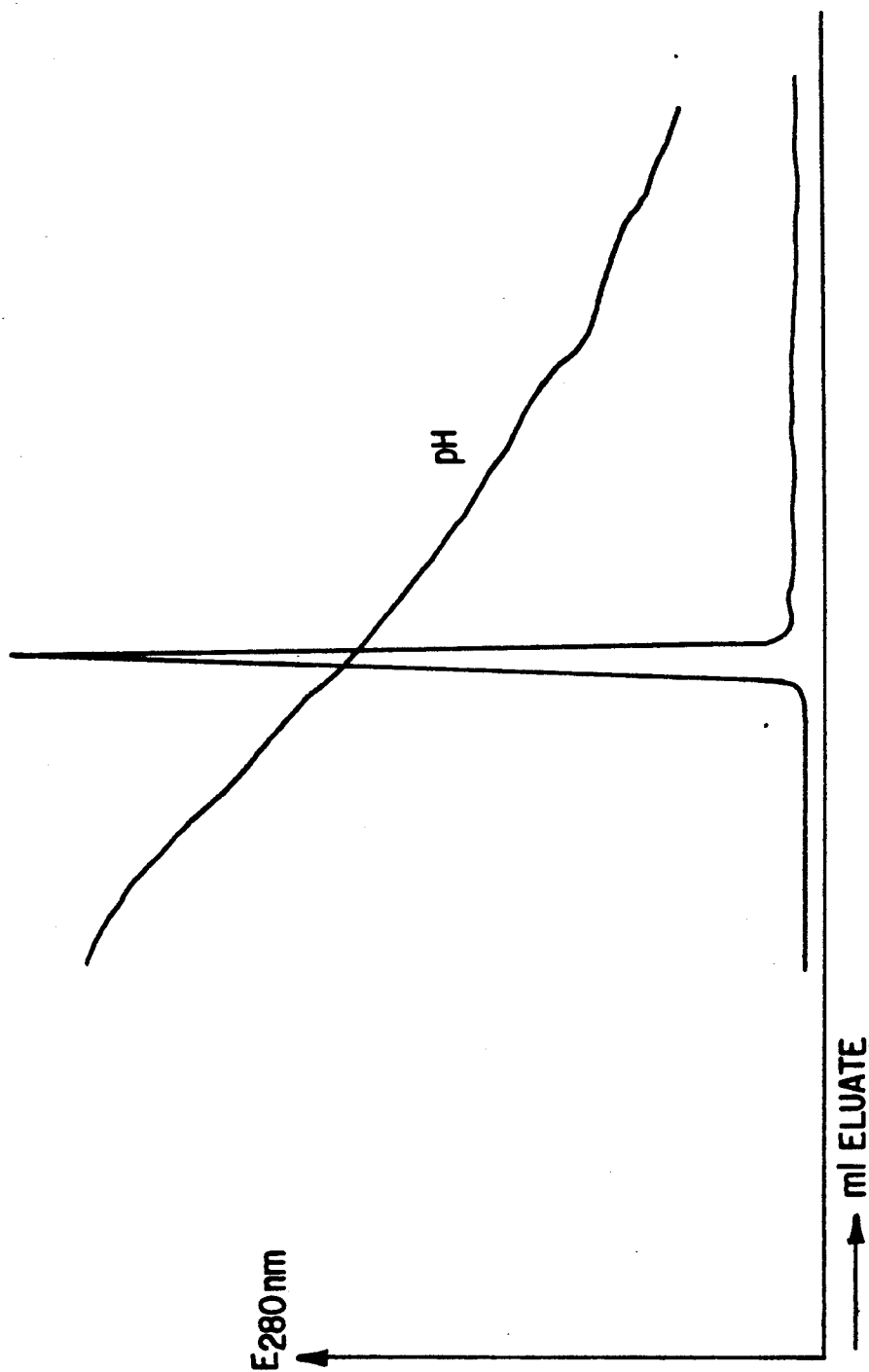
FIG. 10 shows the chromatograph obtained after chromatofocusing of the "main fraction" of the MONO S-peak. A single peak was observed.
Figure 11:
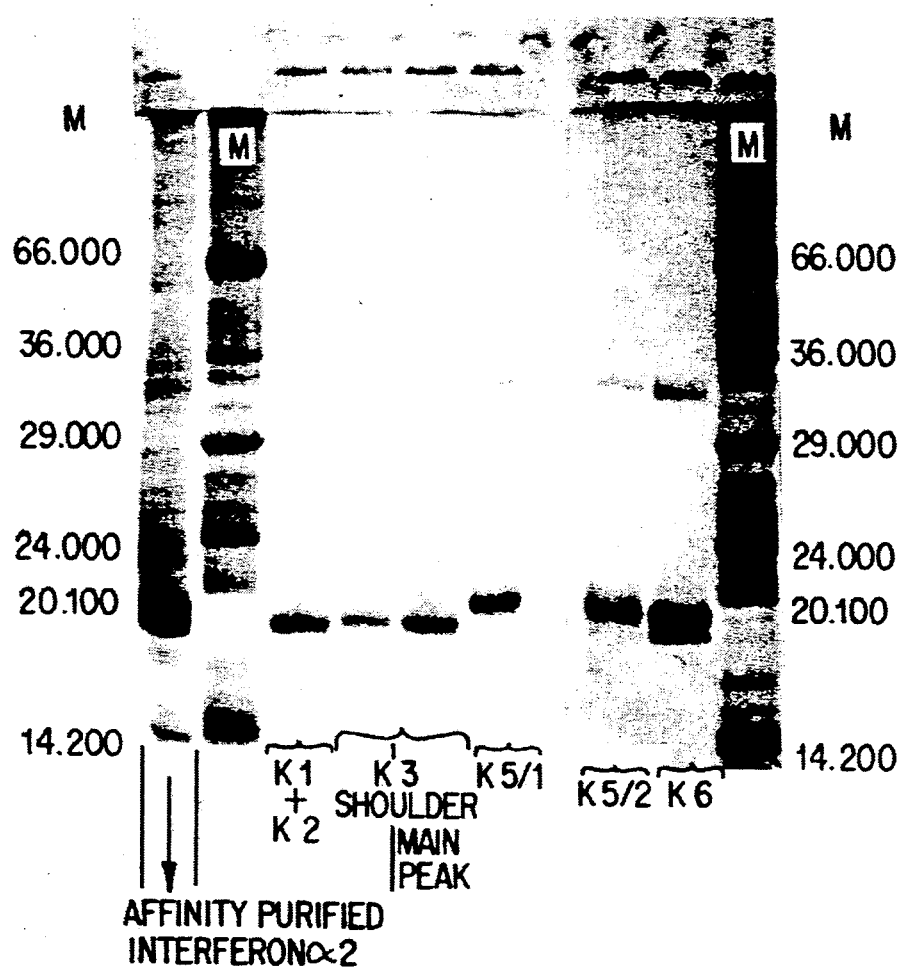
FIG. 11 is a photograph of the pattern obtained after gel electrophoresis of the acid eluate obtained after tandem chromatography and separation of components K1-K7 by reverse phase HPLC. Single bands were obtained for the K1+K2 component, K3 (shoulder and main peak), K5/1 and K5/2, and K6.
Figure 12A:
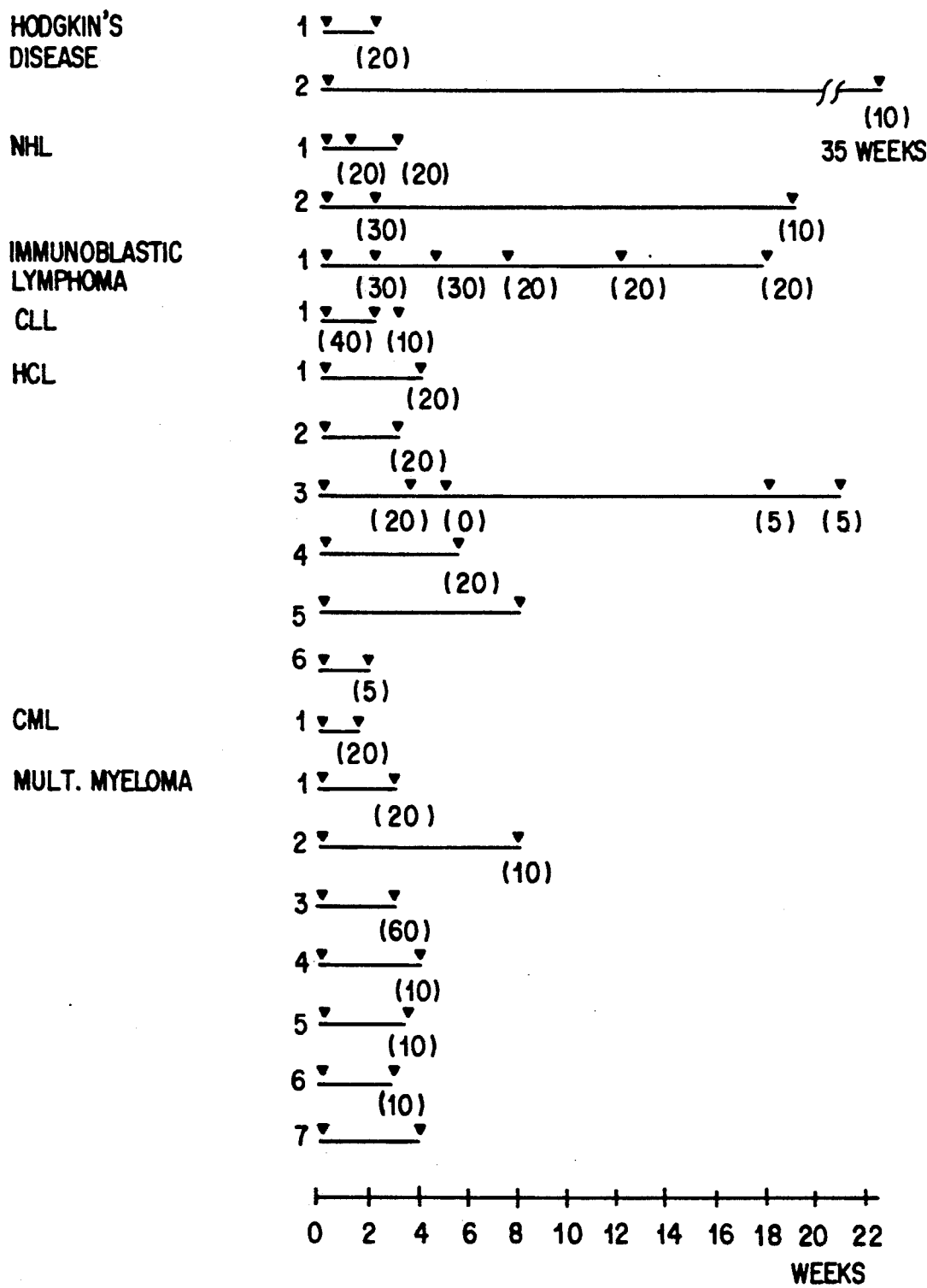
FIGS. 12a-12f present the results of assay for anti-IFN-alpha antibodies in the circulation of patients with various diseases treated with 10 IU/ml IFN alpha/A-599/EMC. The test for anti-IFN-alpha antibodies was a neutralization assay.
Figure 12B:
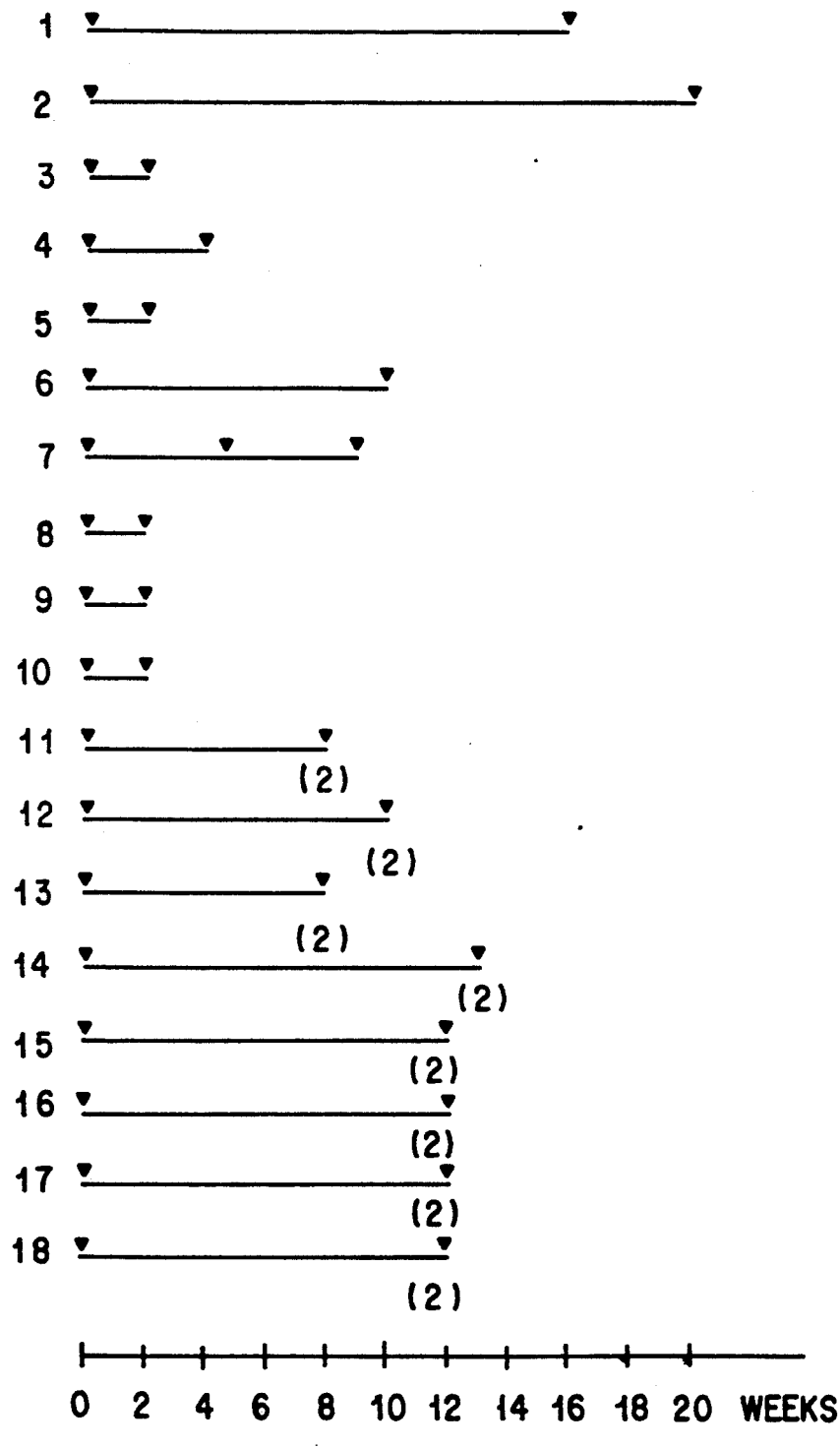
Figure 12C:
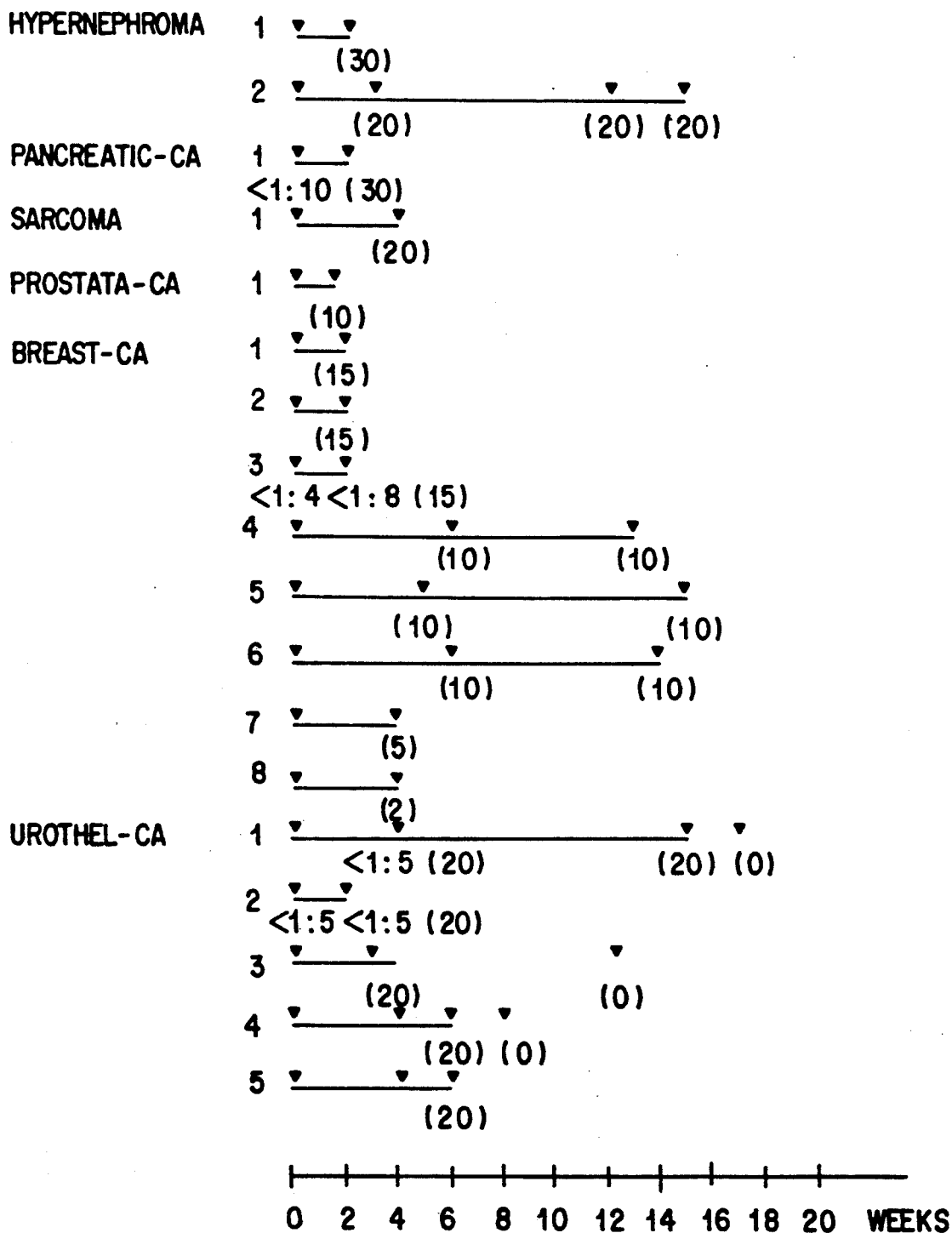
Figure 12D:
Figure 12D:
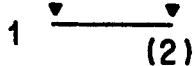
Figure 12F:
Figure 12F:
Figure 12E:
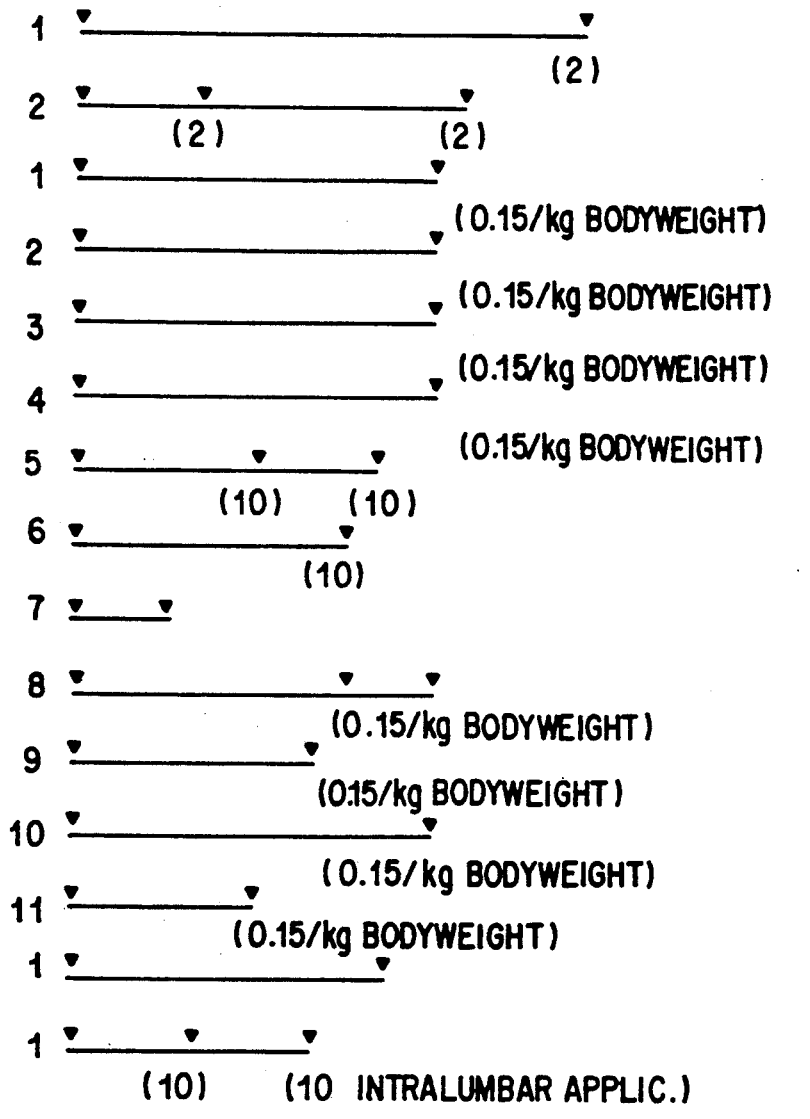

The clear supernatant obtained after precipitation was applied to the column (which had previously been washed with 0.1M ammonium acetate buffer, pH 4.5-5.0), and this column was then washed until the extinction at 280 nm had reverted to the original value. Elution of the adsorbed interferon was carried out with a planar salt gradient by admixing 0.5M ammonium acetate buffer, pH 4.5 to 5.0. Interferon was eluted as a sharp peak. Both the "shoulder" fraction (K3) and the fractions eluted later (K5-K7) were separated from the main peak of pure interferon. The peak of pure interferon was collected and from it aliquots were taken for HPLC analysis (FIGS. 5, 8-11). SDS gel electrophoresis, protein determination, interferon testing and endotoxin determination. A total of 4.1 mg of protein were found in the "shoulder" fraction (9.1 ml); the interferon content was $1.33 \times 10^9$ I.U. (7.7%) (FIGS. 6 and 7). This gave $324 \times 10^6$ I.U./mg of protein.

The main pool of 9.8 ml contained $5.18 \times 10^9$ I.U. (30.3%) of very pure interferon and a total of 16.1 mg of protein; this gave a specific activity of $322 \times 10^6$ I.U./mg of protein.

f;alpha)

The IFN pool was transferred into autoclaved lyo-ampoules (capacity 8 ml) in batches of up to a maximum of 2 ml, corresponding to a quantity of from 1 to about 8 mg of pure interferon per ampoule. The ampoules were then sealed with prewashed and autoclaved lyo-stoppers and cooled to at least $-20°$ C. Lyophilization was carried out at $-10°$ C. under a vacuum of less than 1 torr. After evaporation of the buffer solution, the temperature was increased to 25° C. and lyophilization was continued for at least 1 hour. The vacuum was released and the stoppers were immediately pressed in firmly. After being capped with aluminum seals, the ampoules were then stored in a refrigerator or at $-20°$ C.

f;beta)

To check stability, four different fermentation mixtures were lyophilized after being purified separately from Examples 1a-f;alpha but in a similar manner.

The lyophilized mixtures were dissolved in IRMA dilution buffer and analyzed with the aid of NK2-IRMA for human IFN-alpha (Celltech U.K.)

| Batch | IFN titer before lyophilization | IFN titer after lyophilization | ± % |
|---|---|---|---|
| A | $720 \times 10^6$ | $754 \times 10^6$ | +5 |
| B | $1337 \times 10^6$ | $1526 \times 10^6$ | +14 |
| C | $981 \times 10^6$ | $852 \times 10^6$ | −13 |
| D | $1230 \times 10^6$ | $1149 \times 10^6$ | −7 |

Thus, lyophilization did not cause any losses. After 11 months storage of the lyophilized material at about 4° C. (refrigerator), it was dissolved in 0.1M ammonium acetate and checked for both purity (by gel permeation HPLC) and also for content (by the NK2-IRMA test).

| | Before lyophilization | After 11 months storage in lyophilized form |
|---|---|---|
| Purity (gel-HPLC) | 98.5% | 98.7% |
| IFN titer | $1510 \times 10^6$ units/ml | $1464 \times 10^6$ units/ml |

EXAMPLE 2

To test the effect of the fermentation time on the composition of the interferon components, samples were taken from a fermentation mixture (*E coli* HB101; 28° C.) after 8, 9, 10 or 11 hours, precipitated with acid at pH 2 by the usual method and worked up and analyzed using the method according to the invention. The following table shows the content of K1, K2 and K3 (K1 : Met-IFN, K2: native IFN; K3: non-native IFN) in the samples. The values were determined by chromatofocusing.

| Harvest time after hours | 8 | 9 | 10 | 11 |
|---|---|---|---|---|
| g moist biomass per liter of culture | 14 | 15 | 18 | 21 |
| mg IFN/g biomass (measured in the crude extract) | 0.28 | 0.21 | 0.16 | 0.12 |
| Mg IFN/l of culture volume | 3.9 | 3.2 | 2.9 | 2.5 |
| K1 pI = 5.78 | 0.7% | n.d.* | 10.7% | 19.4% |
| K2 pI = 5.64 | 96.2% | 97.5% | 86.1% | 78.5% |
| K3 pI = 5.49 | 3.1% | 2.5% | 3.3% | 2.1% |

*n.d. = not detected.

EXAMPLE 3

Coupling of the EBI 1 antibody to CNRr-activated Sepharose 4B (cf. DE-OS 33 06 060)

The EBI-1 antibody was first dissolved with 0.5M NaCl/0.2M NaHCO$_3$, pH 8.4 (in as little buffer as possible) and dialized with the buffer until no further sulfate ions could be detected in the external solution (barium chloride test). Careful removal of the ammonium sulfate was absolutely essential as ammonium ions disrupt the subsequent coupling to the carrier. The protein concentration was then adjusted to 5 mg/ml with buffer. For the coupling, CNBr-activated Sepharose 4B (Pharmacia) was used as carrier. It was first given a preliminary wash in accordance with the manufacturer's instructions (leaflet enclosed with the package). One gram of activated Sepharose was used for every 25 mg of EBI-1 antibody. Coupling was carried out in the above buffer at pH 8.4 for 2 hours at ambient temperature. Then the EBI-1 Sepharose was removed by suction filtering and washed in accordance with the instruction leaflet. Not more than 5% of the EBI-1 antibody used should remain in the filtrate. The finished EBI-1 Sepharose was stored in PBS/azide in a cold store.

The composition of PBS/azide is: PBS:
7.30 g sodium chloride p.A. (Merck 6404)
3.00 g Na$_2$HPO$_4 \times$ 2H$_2$O p.A. (Merck 6580)
1.15 g NaH$_2$PO$_4 \times$ H$_2$O p.A. (Merck 6346 dissolved and made up to 1000 ml; pH 7.0)
Azide: 1.0 g/l of very pure sodium azide (Merck 6688) were added to the PBS.

The finished solution was filtered sterile (0.2 micron pore size) and stored in a refrigerator.

The Interferon Antibody Assay (Neutralization Assay) conditions are:

Materials

Cells
Human lung carcinoma cells "A-549" ATCC CCL 185.
Virus
Encephalomyocarditis virus (EMC), ATCC VR 129.
Interferon Standard
HS-11 (1 ampoule "HS-11" =lyophilized Hu IFN ralpha-A taken up in 1.2 ml H$_2$O, yielding 12,000 IU/ml)
Tissue Culture Plates
96 wells with lid, flat bottom, Corning, N.Y., No. 25860, diameter of well 6.4 mm, tissue culture treated.
Media DMEM=Dulbecco's modified Eagle medium with glutamine, without sodium bicarbonate, Flow cat. no. 10-331-24 (1F-017D)

HEPES: Sigma No. H-3375

TRICINE: Calbiochem No. 33468, A grade

FCS=fetal calf serum, Boehringer Mannheim

HUMAN SERUM-ALBUMIN Behring Inst., 20%, for infusion

Antibiotic, tiamulin hydrogen fumarate, Biochemie Kundl/Triol, Austria (Sandoz C.)

Growth medium: DMEM+10 FCS/deactivated 30 min/56° C.

| |
|---|
| +13 mM HEPES |
| +6 mM TRICINE |
| +1.6 g/l NaHCO$_3$ |
| without antibiotics |
| pH 7.2-7.4 |

Assay medium: same as growth medium but 5% FCS instead of 10% and with the addition of 5 μg of tiamulin/ml Dilution medium: growth medium with no serum but with 5 μg/ml of tiamulin Virus medium: growth medium with no serum but with 5 μg/ml of tiamulin and 3.5 mg/ml of human serum albumin

| Methyl violet storage solution: | |
|---|---|
| methyl violet (Merck No. 1402) | 50 ml |
| ethanol (abs) | 100 ml |
| dissolved and filtered for at about 50° C. | |
| methyl violet solution for use | |
| storage solution | 50 ml |
| water (pH neutral) | 950 ml |

The cells were treated as a permanent cell line. They were propagated by trypsinization and dilution in growth medium. For the assay, the cells were counted in a hemocytometer and suspended in assay medium in order to obtain an inoculation solution of 4–5×10$^4$ cells per ml per well; these were distributed into the dishes. Incubation was carried out in an atmosphere consisting of 5% CO$_2$ in air and 80% relative humidity, at 37° C. After 8-24 hours, the mono-layer was usually complete. At this time, the interferon and the serum dilutions were prepared in separate test tubes.

For the control dish, HS-11 dilutions of 1:1000, 1:2000 up to 1:32,000 were incubated for 1 hour at 37° C.

For the test dish, the serum samples were diluted to 1:2, 1:4, 1:8 and so on up to 1:64 with a dilution medium which contained sufficient HS-11 to give a final concentration of 10 iU HS-11/ml in each glass and then incubated for 1 hour at 37° C.

The dishes were decanted and each well was filled with 100 ml of the dilution medium (series 2, 3, 10 and 11) or with 100 μl of the dilutions (series 4–9). The dishes were incubated at 37° C. for 4 hours as above. Then the dishes were given a coating of 100 μl of virus medium (without the virus) for each and 50 μl of the virus dilution (series 3, 11, 4–9) in order to achieve a cytopathic effect of approximately 90% within 36 hours and then incubated again. After 24 hours and microscopic monitoring the cells were stained with methyl violet.

The results are shown in FIGS. 12a-12f; the diagram appears in FIG. 13.

METHOD

The following methods were used for the analysis:

Protein Determination

BioRad Protein Assay: This assay uses the dye Coomassie brilliant blue and measure the protein/dye complex at 595 nm. The standard used is bovine serum albumin.

Planimetric determination of the peak surfaces measured at 214 nm which were recorded by gel permeation HPLC. The results are converted with the aid of a factor from the calibrating substances bovine serum albumin, ovalbumin, trypsinogen and lysozyme. This measurement was carried out particularly on the preparations after the Tandem Chromatography purification stage, pH 4.5, precipitation and FPLC on MONO-S, additionally or exclusively.

Interferon determination: The "NH$_2$-IRMA" for human alpha interferon, commercially available from Celltech (U.K.), was used. The standard used was a laboratory standard "HS 11" which was adjusted to International Standard B 69/19 by biological assay (plaque reduction test WISH cells and vesicular stomatitis virus).

SDS-gel electrophoresis: The method of Laemmli (Nature 227, 680 (1980)) was used. The dye used to stain the proteins was Coomassie brilliant blue. 20 micrograms of the interferon preparation were used in the purity checks.

Chromatofocusing: The method of Bodo and Adolf (Sepration and Characterization of Human IFN-alpha Subtypes in the Biology of the Interferon System, Eds. E. DeMayer and H. Schellekens, Elsevier, 1983, pp. 113–118) was used, with a MONO-P chromatofocusing column HR 5/20 (Pharmacia) in a pH range of 4-7. The buffers contained 25% acetonitrile instead of the specified 25% 1,2-propandiol in order to increase the flow rate. The protein concentration was recorded at 280 nm, and the pH was recorded automatically. The samples to be analyzed were lyophilized, dissolved in water in amounts of 1 mg/ml and then diluted with 5 volumes of buffer A (pH 7.1). Amounts of interferon used for each analysis were 0.2–1.0 mg.

Gel Permeation HPLC (High Pressure Liquid Chromatography)

Stationary Phase

WATERS I-125; 2× (300 mm×7.8 mm);

10 μm particle diameter

Mobile Phase:

0.5M Na$_2$SO$_4$ 0.02M NaH$_2$PO adjusted to pH 7.0 with NaOH 0.04% Tween 20

25% propyleneglycol

Flow speed 0.5 ml/min

Detection

UV absorption at 214 nm

| Molecular weight calibration: | |
|---|---|
| Bovine serum albumin | M 66,000 |
| Ovalbumin | M 45,000 |
| Trypsinogen | M 24,000 |
| Lysozyme | M 14,300 |

Reverse Phase HPLC (High Pressure Liquid Chromatography)

Stationary Phase
Bakerbond WP C 18; 250 mm×4.6 mm;
5 μm particle diameter;
30 nm pore diameter
Mobile Phase
A: 0.1% fluoroacetic acid in water, pH 2.2
B: 0.1% trifluoroacetic acid in acetonitrile Gradient Program
0–2 min: 45% B 2–32 min: 45–53% B
32–40 min: 53% B
40–50 min: 45% B
Flow Speed
1 ml/min
Detection
UV absorption at 214 nm What is new and desired to be covered by the Letters Patent:

1. A process for the preparation and purification of recombinant alpha-interferon, which comprises:
cultivating *E. coli* containing the interferon gene for a growth period during which not more than 5% methionine-interferon is formed;
extracting and concentrating the expressed interferon;
subjecting the concentrated material to Tandem Chromatography, wherein said Tandem Chromatography comprises separation on a cellulose column followed by an anti-alpha-interferon monoclonal antibody affinity column;
subjecting the affinity purified material to isoelectric precipitation of impurities at about pH 4.0 to about pH 4.8; and
purifying the interferon by chromatography on a high performance cation exchange column using a volatile buffer, wherein said purified interferon is non-immunogenic when administered parenterally to a human.

2. The process of claim 1, wherein said recombinant alpha-interferon has the amino acid sequence:

| Cys | Asp | Leu | Pro | Gln | Thr | His | Ser | Leu | Gly | Ser | Arg |
|---|---|---|---|---|---|---|---|---|---|---|---|
| Arg | Thr | Leu | Met | Leu | Leu | Ala | Gln | Met | Arg | Arg | Ile |
| Ser | Leu | Phe | Ser | Cys | Leu | Lys | Asp | Arg | Arg | Asp | Phe |
| Gly | Phe | Pro | Gln | Glu | Glu | Phe | Gly | Asn | Gln | Phe | Gln |
| Lys | Ala | Glu | Thr | Ile | Pro | Val | Leu | His | Glu | Met | Ile |
| Gln | Gln | Ile | Phe | Asn | Leu | Phe | Ser | Thr | Lys | Asp | Ser |
| Ser | Ala | Ala | Trp | Asp | Glu | Thr | Leu | Leu | Asp | Lys | Phe |
| Tyr | Thr | Glu | Leu | Tyr | Gln | Gln | Leu | Asn | Asp | Leu | Glu |
| Ala | Cys | Val | Ile | Gln | Gly | Val | Gly | Val | Thr | Glu | Thr |
| Pro | Leu | Met | Lys | Glu | Asp | Ser | Ile | Leu | Ala | Val | Arg |
| Lys | Tyr | Phe | Gln | Arg | Ile | Thr | Leu | Tyr | Leu | Lys | Glu |
| Lys | Lys | Tyr | Ser | Pro | Cys | Ala | Trp | Glu | Val | Val | Arg |
| Ala | Glu | Ile | Met | Arg | Ser | Phe | Ser | Leu | Ser | Thr | Asn |
| Leu | Gln | Glu | Ser | Leu | Arg | Ser | Lys | Glu | | | |

3. The process of claim 1, wherein said recombinant alpha-interferon has the amino acid sequence;

| Cys | Asp | Leu | Pro | Gln | Thr | His | Ser | Leu | Gly | Ser | Arg |
|---|---|---|---|---|---|---|---|---|---|---|---|
| Arg | Thr | Leu | Met | Leu | Leu | Ala | Gln | Met | Arg | Arg | Ile |
| Ser | Leu | Phe | Ser | Cys | Leu | Lys | Asp | Arg | Arg | Asp | Phe |
| Gly | Phe | Pro | Gln | Glu | Glu | Phe | Gly | Asn | Gln | Phe | Gln |
| Lys | Ala | Glu | Thr | Ile | Pro | Val | Leu | His | Glu | Met | Ile |
| Gln | Gln | Ile | Phe | Asn | Leu | Phe | Ser | Thr | Lys | Asp | Ser |
| Ser | Ala | Ala | Trp | Asp | Glu | Thr | Leu | Leu | Asp | Lys | Phe |
| Tyr | Thr | Glu | Leu | Tyr | Gln | Gln | Leu | Asn | Asp | Leu | Glu |
| Ala | Cys | Val | Ile | Gln | Gly | Val | Gly | Val | Thr | Glu | Thr |
| Pro | Leu | Met | Lys | Glu | Asp | Ser | Ile | Leu | Ala | Val | Arg |
| Lys | Tyr | Phe | Gln | Arg | Ile | Thr | Leu | Tyr | Leu | Lys | Glu |
| Lys | Lys | Tyr | Ser | Pro | Cys | Ala | Trp | Glu | Val | Val | Arg |
| Ala | Glu | Ile | Met | Arg | Ser | Phe | Ser | Leu | Ser | Thr | Asn |
| Leu | Gln | Glu | Ser | Leu | Arg | Ser | Lys | Glu | | | | and a pure native monomeric form contains disulfide bridges between the cystein residues at positions 1 and 98, and 29 and 138.

4. The process of claim 1, wherein said cellulose column comprises a DE-52 cellulose column.

5. The process of claim 1 wherein said affinity column comprises a column containing an anti-alpha-interferon monoclonal IgG antibody coupled to a carrier.

6. The process of claim 1, wherein said cation exchange column comprises a fast protein liquid chromatography column comprising strong cation exchanging hydrophilic polymer beads packed into a column.

7. The process of claim 1, wherein said recombinant alpha-interferon contains less than 5% methionine interferon, is free from reduced forms and fragments of interferon, contains less than 0.2% oligomer and less than 2% dimers, timers, and tetramers, and wherein over 90% of the monomer content consists of native, monomeric interferon.

8. The process of claim 1, wherein said recombinant alpha-interferon comprises homogeneous, human alpha-interferon with the amino acid sequence;

| Cys | Asp | Leu | Pro | Gln | Thr | His | Ser | Leu | Gly | Ser | Arg |
|---|---|---|---|---|---|---|---|---|---|---|---|
| Arg | Thr | Leu | Met | Leu | Leu | Ala | Gln | Met | Arg | Arg | Ile |
| Ser | Leu | Phe | Ser | Cys | Leu | Lys | Asp | Arg | Arg | Asp | Phe |
| Gly | Phe | Pro | Gln | Glu | Glu | Phe | Gly | Asn | Gln | Phe | Gln |

-continued

| Lys | Ala | Glu | Thr | Ile | Pro | Val | Leu | His | Glu | Met | Ile |
| Gln | Gln | Ile | Phe | Asn | Leu | Phe | Ser | Thr | Lys | Asp | Ser |
| Ser | Ala | Ala | Trp | Asp | Glu | Thr | Leu | Leu | Asp | Lys | Phe |
| Tyr | Thr | Glu | Leu | Tyr | Gln | Gln | Leu | Asp | Asp | Leu | Glu |
| Ala | Cys | Val | Ile | Gln | Gly | Val | Gly | Val | Thr | Glu | Thr |
| Pro | Leu | Met | Lys | Glu | Asp | Ser | Ile | Leu | Ala | Val | Arg |
| Lys | Tyr | Phe | Gln | Arg | Ile | Thr | Leu | Tyr | Leu | Lys | Glu |
| Lys | Lys | Tyr | Ser | Pro | Cys | Ala | Trp | Glu | Val | Val | Arg |
| Ala | Glu | Ile | Met | Arg | Ser | Phe | Ser | Leu | Ser | Thr | Asn |
| Leu | Gln | Glu | Ser | Leu | Arg | Ser | Lys | Glu | | | | comprising less than 5% methionine-interferon, free from reduced forms and fragments of said alpha-interferon, containing less than 0.2% oligomer, and less than 2% dimers, trimers, and tetramers, and wherein the native monomeric alpha-interferon contains disulfide bridges between the cysteine residues at positions 1 and 98, and 29 and 138.

* * * * *